US010767200B2

(12) United States Patent
Suzuki et al.

(10) Patent No.: US 10,767,200 B2
(45) Date of Patent: Sep. 8, 2020

(54) METHOD FOR PRODUCING L-AMINO ACID

(71) Applicant: AJINOMOTO CO., INC., Tokyo (JP)

(72) Inventors: Kisho Suzuki, Kanagawa (JP);
Masayuki Mori, Kanagawa (JP);
Takehiro Hiura, Kanagawa (JP);
Nobuaki Matsuoka, Kanagawa (JP);
Takehiko Chikamori, Kanagawa (JP)

(73) Assignee: AJINOMOTO CO., INC., Tokyo (JP)

( * ) Notice: Subject to any disclaimer, the term of this patent is extended or adjusted under 35 U.S.C. 154(b) by 203 days.

(21) Appl. No.: 16/111,395

(22) Filed: Aug. 24, 2018

(65) Prior Publication Data

US 2019/0040429 A1  Feb. 7, 2019

Related U.S. Application Data

(63) Continuation of application No. PCT/JP2017/007014, filed on Feb. 24, 2017.

(30) Foreign Application Priority Data

Feb. 24, 2016  (JP) ................ 2016-033636

(51) Int. Cl.
| C12P 13/08 | (2006.01) |
| C12N 1/20 | (2006.01) |
| C12R 1/15 | (2006.01) |
| C12R 1/19 | (2006.01) |

(52) U.S. Cl.
CPC .............. *C12P 13/08* (2013.01); *C12N 1/20* (2013.01); *C12R 1/15* (2013.01); *C12R 1/19* (2013.01)

(58) Field of Classification Search
CPC .......... A23V 2002/00; A23V 2200/324; C12N 1/20; C12N 2500/33; C12N 2500/60; C12N 2710/18071; C12N 2710/24132; C12N 7/00; A23C 9/1238; A23C 9/137; A23K 10/16; A23K 10/18; A23K 50/10; A23K 50/20; A23K 50/30; A23K 50/40; A23K 50/70; A23K 50/75; A23K 50/80; A23L 27/21; A23L 27/215; A23L 27/24; A23Y 2220/03; A23Y 2220/15; A23Y 2220/39; A23Y 2240/75; A61K 2035/11; A61K 2039/505; A61K 2039/545; A61K 2039/58; A61K 35/74; A61K 35/744; A61K 35/747; A61K 35/768; A61K 39/025; A61K 39/05; A61K 39/092; A61K 39/107; A61K 39/39; A61K 39/3955; A61K 47/44; A61P 37/04; C02F 2203/004; C02F 2301/106; C02F 3/006; C02F 3/34; C02F 3/341; C02F 3/348;
C07K 14/00; C07K 14/001; C07K 16/18; C11D 3/3719; C11D 3/38; C11D 3/386; C12P 13/08; C12P 13/10; C12R 1/15; C12R 1/19
See application file for complete search history.

(56) References Cited

U.S. PATENT DOCUMENTS

| 5,770,409 A | 6/1998 | Pfefferle et al. |
| 5,912,113 A | 6/1999 | Nakamura et al. |
| 6,025,169 A | 2/2000 | Nakamura et al. |
| 6,133,000 A | 10/2000 | Pfefferle et al. |
| 2002/0025564 A1 | 2/2002 | Kobayashi et al. |
| 2003/0152633 A1 | 8/2003 | Kushiki et al. |
| 2007/0243590 A1 | 10/2007 | Takeshita et al. |
| 2011/0281311 A1 | 11/2011 | Wakasa et al. |
| 2012/0296117 A1 | 11/2012 | Wu |
| 2012/0302788 A1 | 11/2012 | Garcia et al. |
| 2015/0337254 A1 | 11/2015 | Takeshita |

FOREIGN PATENT DOCUMENTS

| JP | 60-94094 A | 5/1985 |
| JP | 5-30985 A | 2/1993 |
| JP | 5-244969 A | 9/1993 |
| JP | 2002-065287 A | 3/2002 |
| JP | 2003-219807 A | 8/2003 |
| JP | 2012-029565 A | 2/2012 |
| JP | 2013-514357 A | 4/2013 |
| JP | 2013-514362 A | 4/2013 |
| WO | WO2006/038695 A1 | 4/2006 |

OTHER PUBLICATIONS

Extended European Search Report for European Patent App. No. 17756623.9 (dated Sep. 6, 2019).
Hussain, A., et al., "Optimization of Fermentation Medium for L-Lysine Production by Corynebacterium Glutamicum," Pak. J. Bot. 2015;47(SI):345-349.
Notification of Transmittal of Copies of Translation of the International Preliminary Report on Patentability for PCT Patent App. No. PCT/JP2017/007014 (dated Sep. 7, 2018).
International Search Report and Written Opinion for PCT Patent App. No. PCT/JP2017/007014 (dated May 16, 2017) with English translation of the ISR.

*Primary Examiner* — Deborah H Ware
(74) *Attorney, Agent, or Firm* — Cermak Nakajima & McGowan LLP; Shelly Guest Cermak

(57) ABSTRACT

A method for producing a basic acid such as L-lysine is provided. A basic amino acid or a fermentation product containing the same is produced by a method including the following steps (A) and (B): (A) a step of culturing a microorganism able to produce a basic amino acid in a culture medium so that bicarbonate ions and/or carbonate ions serve as counter ions for the basic amino acid, to obtain a fermentation broth containing the basic amino acid; (B) a step of subjecting the fermentation broth to a heat treatment under a pressure sufficient for preventing generation of carbon dioxide gas from the fermentation broth.

19 Claims, 5 Drawing Sheets

METHOD FOR PRODUCING L-AMINO ACID

This application is a Continuation of, and claims priority under 35 U.S.C. § 120 to, International Application No. PCT/JP2017/007014, filed Feb. 24, 2017, and claims priority therethrough under 35 U.S.C. § 119 to Japanese Patent Application No. 2016-033636, filed Feb. 24, 2016, the entireties of which are incorporated by reference herein.

BACKGROUND OF THE INVENTION

Field of the Invention

The present invention relates to a method for producing an L-amino acid, specifically a basic amino acid such as L-lysine and L-arginine, by fermentation using a microorganism. L-Amino acids are industrially useful as additives for animal feeds, ingredients for seasonings, foods and drinks, amino acid infusions, and so forth.

Brief Description of the Related Art

L-Amino acids such as basic amino acids are industrially produced by, for example, fermentation using microorganisms having an L-amino acid-producing ability. In a method for producing a basic amino acid by fermentation, a microorganism having a basic amino acid-producing ability is cultured to generate and accumulate the basic amino acid in a fermentation broth, and the basic amino acid is collected from the fermentation broth. In such a case, the cultivation is carried out by a batch method, a fed-batch method, or a continuous method.

In production of a basic amino acid by fermentation, sulfate ions or chloride ions have been conventionally used as counter anions of the basic amino acid for maintaining the pH of a culture medium (JP05-030985A and JP05-244969A). However, there is still room for improvement in methods using sulfate ions or chloride ions from the viewpoint of the purification cost and corrosion of a fermentation tank.

When purification is required, a basic amino acid is often collected from the fermentation broth by ion-exchange. For example, in the case of L-lysine, the fermentation broth is adjusted to an acidic pH, and L-lysine is adsorbed onto an ion-exchange resin, then eluted from the resin with ammonium ions, and used as lysine base as it is, or crystalized as L-lysine hydrochloride with hydrochloric acid.

By contrast, when purification is not required, generally, the fermentation broth is concentrated as it is, or the fermentation broth adjusted to an acidic pH with hydrochloric acid or sulfuric acid is subject to spray granulation. In such a case, the content ratio of the basic amino acid in the fermentation product is limited due to the remaining component(s) that are present in the culture medium, and hence, counter anions added to the culture medium cannot be ignored. Therefore, a reduction in the amount of counter anions used is important from the viewpoint not only of the production cost but also of the quality of the product.

To reduce the amount of counter anions used in methods of producing a basic amino acid by fermentation, bicarbonate ions and/or carbonate ions can be used as counter ions of the basic amino acid (also referred to as "carbonate fermentation"; US2002-025564A and WO2006/038695). In the carbonate fermentation, a basic amino acid can be produced by fermentation while reducing the amount of sulfate ions and/or chloride ions that are required. In addition, when purification is required, decarboxylation can be carried out by raising the temperature or adjusting the pH to an acidic pH, to easily obtain a lysine base solution.

SUMMARY OF THE INVENTION

Fermentation broths of an amino acid are often subject to a heat treatment. For example, a heat treatment is carried out for the purpose of sterilization or concentration, and furthermore, other treatments such as cell removal and ion-exchange resin treatment are often carried out at a high temperature from the viewpoint of improvement in the productivity. It has been found that when a carbonate fermentation broth of lysine is heated, the amount of lysine present decreased (see Tables 1 and 2). It was further found that when a carbonate fermentation broth of lysine was heated, bicarbonate ions and/or carbonate ions used as counter ions were released as carbon dioxide gas to thereby raise the pH, and that a higher pH resulted in a higher ratio of decrease in the amount of lysine present (Table 3).

Such a decrease in the amount of the basic amino acid present can be prevented by decreasing the pH of the fermentation broth with hydrochloric acid or sulfuric acid. However, in such a case, the advantageous feature of the carbonate fermentation that the amount of sulfate ions and/or chloride ions can be reduced is cancelled out at the purification stage. Hence, a novel technique was developed to prevent a decrease in the amount of basic amino acid present in the fermentation broth during the carbonate fermentation, and thereby a method for efficiently producing a basic amino acid or a fermentation product containing the same is described.

When the fermentation broth obtained by carbonate fermentation is subject to a heat treatment, a decrease in the amount of basic amino acid can be prevented by carrying out the heat treatment under a pressure sufficient to prevent generation of carbon dioxide gas from the fermentation broth.

It is an aspect of the present invention to provide a method for producing a basic amino acid or a fermentation product containing the basic amino acid, the method comprising the following steps: (A) culturing a microorganism able to produce a basic amino acid in a culture medium so that bicarbonate ions and/or carbonate ions serve as counter ions for the basic amino acid, to obtain a fermentation broth containing the basic amino acid; and (B) heat treating the fermentation broth under a pressure sufficient to prevent generation of carbon dioxide gas from the fermentation broth.

It is a further aspect of the present invention to provide method as described above, wherein said pressure is gauge pressure and is equal to or higher than the total value of the partial pressure of carbon dioxide and the partial pressure of water vapor at the temperature of the heat treatment in terms of gauge pressure, and wherein the partial pressure of carbon dioxide is determined using the concentrations of the basic amino acid, $CO_2$, $NH_3$, K, Mg, Cl, $SO_4$, acetic acid, and succinic acid present in the fermentation broth and the temperature of the heat treating as variables.

It is a further aspect of the present invention to provide method as described above, wherein said pressure is gauge pressure and is equal to or higher than the pressure shown in the following equation: Pressure $(kPa) = 1.99 \times 10^{-3} \times T^{2.54}$, wherein T is the temperature in centigrade of the heat treating.

It is a further aspect of the present invention to provide method as described above, wherein said pressure is gauge pressure and is equal to or higher than the pressure of a gas phase in a sealed vessel observed when the fermentation broth is present in the sealed vessel so that the porosity of said vessel becomes 6% v/v and adjusted to the temperature of said heat treating.

It is a further aspect of the present invention to provide method as described above, wherein said pressure is gauge pressure and is 400 kPa or higher.

It is a further aspect of the present invention to provide method as described above, wherein said pressure is gauge pressure and is 1000 kPa or higher.

It is a further aspect of the present invention to provide method as described above, wherein the temperature of the heat treating is 80° C. to 130° C.

It is a further aspect of the present invention to provide method as described above, wherein the temperature of the heat treating is 100° C. to 130° C.

It is a further aspect of the present invention to provide method as described above, wherein said heat treating is carried out in a pressure vessel under conditions wherein substantially no gas phase is present in the pressure vessel.

It is a further aspect of the present invention to provide method as described above, further comprising: decarboxylating the fermentation broth after said heat treating.

It is a further aspect of the present invention to provide method as described above, wherein said culturing is carried out while controlling the pH of the culture medium to 7.2 to 9.0 during at least a partial period of culture.

It is a further aspect of the present invention to provide method as described above, wherein said culturing is carried out so that the pH of the culture medium at the completion of culture is 7.2 or higher.

It is a further aspect of the present invention to provide method as described above, wherein said culturing is carried out so that bicarbonate ions and/or carbonate ions are present in the culture medium at a concentration of 20 mM or more during at least a partial period of culture by controlling the internal pressure of a fermentation tank to be positive and/or by supplying carbon dioxide gas into the culture medium.

It is a further aspect of the present invention to provide method as described above, wherein said culturing is carried out so that the concentration of anions other than bicarbonate ions and/or carbonate ions in the culture medium is 900 mM or lower.

It is a further aspect of the present invention to provide method as described above, wherein the internal gauge pressure of the fermentation tank is 0.03 to 0.2 MPa.

It is a further aspect of the present invention to provide method as described above, wherein said culturing is carried out so that the total ammonia concentration in the culture medium is controlled to 300 mM or lower during at least a partial period of culture.

It is a further aspect of the present invention to provide method as described above, wherein the basic amino acid is L-lysine.

It is a further aspect of the present invention to provide method as described above, wherein the microorganism is a coryneform bacterium or *Escherichia coli*.

It is a further aspect of the present invention to provide method as described above, wherein said fermentation product is selected from the group consisting of the fermentation broth, a supernatant of the fermentation broth, a decarboxylation product of the fermentation broth, a concentrated product of the fermentation broth, a dried product of the fermentation broth, and a processed product of the fermentation broth.

DETAILED DESCRIPTION OF EXEMPLARY EMBODIMENTS

Figure 1:
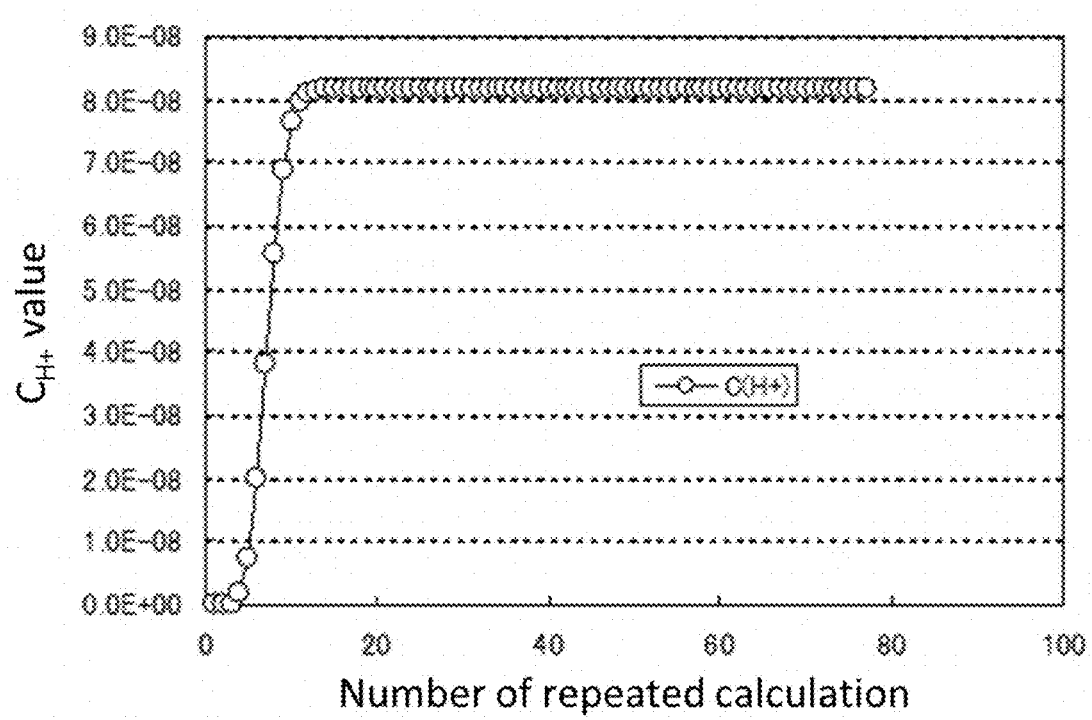
FIG. 1 is a diagram showing the change of $C_{H+}$ when carrying out repeated calculation based on Newton's method.

The method as described herein is a method for producing a basic amino acid or a fermentation product containing the same, the method including the following steps (A) and (B): (A) a step of culturing a microorganism able to produce a basic amino acid in a culture medium so that bicarbonate ions and/or carbonate ions serve as counter ions for the basic amino acid, to obtain a fermentation broth containing the basic amino acid; (B) a step of subjecting the fermentation broth to a heat treatment under a pressure sufficient to prevent generation of carbon dioxide gas from the fermentation broth. The step (A) can also be referred to as the "fermentation step". The step (B) can also be referred to as the "pressurized heat treatment step". The fermentation broth containing a basic amino acid obtained in the step (A) can also be referred to simply as the "fermentation broth". The microorganism able to produce a basic amino acid can also be referred to as the "basic amino acid-producing microorganism".

Examples of the basic amino acid can include L-lysine, L-arginine, and L-histidine. L-lysine is a particular example. A single kind of basic amino acid may be produced, or two or more kinds of basic amino acids may be produced. In addition, the fermentation product may contain a single kind of basic amino acid, or two or more kinds of basic amino acids. Each basic amino acid can be an L-isomer, unless otherwise stated.

<1> Microorganism Having Basic Acid-Producing Ability

<1-1> Microorganism Having Basic Acid-Producing Ability

The term "microorganism able to produce a basic amino acid (basic amino acid-producing microorganism)" can refer to a microorganism having an ability to generate and accumulate an objective basic amino acid in a culture medium to such a degree that the basic amino acid can be collected from the medium, when the microorganism is cultured in the culture medium. The microorganism having a basic amino acid-producing ability may be a microorganism that is able to accumulate an objective basic amino acid in a culture medium in an amount of 0.5 g/L or more, or 1.0 g/L or more. The microorganism having a basic amino acid-producing ability may produce a single kind of a basic amino acid, or two or more kinds of basic amino acids.

The microorganism having a basic amino acid-producing ability is not particularly limited, so long as it is able to produce a basic amino by carbonate fermentation. Examples of the microorganism can include bacteria and yeasts. Bacteria are are particular examples. Examples of bacteria can include coryneform bacteria, bacteria belonging to the genus *Escherichia*, bacteria belonging to the genus *Serratia*, and bacteria belonging to the genus *Bacillus*.

Examples of the coryneform bacteria can include bacteria belonging to the genus *Corynebacterium*, *Brevibacterium*, *Microbacterium*, or the like.

Specific examples of the coryneform bacteria can include the following species.

*Corynebacterium acetoacidophilum*
*Corynebacterium acetoglutamicum*
*Corynebacterium alkanolyticum*
*Corynebacterium callunae*
*Corynebacterium crenatum*
*Corynebacterium glutamicum*
*Corynebacterium lilium*
*Corynebacterium melassecola*
*Corynebacterium thermoaminogenes (Corynebacterium efficiens)*
*Corynebacterium herculis*
*Brevibacterium divaricatum (Corynebacterium glutamicum)*
*Brevibacterium flavum (Corynebacterium glutamicum)*
*Brevibacterium immariophilum*
*Brevibacterium lactofermentum (Corynebacterium glutamicum)*
*Brevibacterium roseum*
*Brevibacterium saccharolyticum*
*Brevibacterium thiogenitalis*
*Corynebacterium ammoniagenes (Corynebacterium stationis)*
*Brevibacterium album*
*Brevibacterium cerinum*
*Microbacterium ammoniaphilum*

Specific examples of the coryneform bacteria can include the following strains.

*Corynebacterium acetoacidophilum* ATCC 13870
*Corynebacterium acetoglutamicum* ATCC 15806
*Corynebacterium alkanolyticum* ATCC 21511
*Corynebacterium callunae* ATCC 15991
*Corynebacterium crenatum* AS1.542
*Corynebacterium glutamicum* ATCC 13020, ATCC 13032, ATCC 13060, ATCC 13869, FERM BP-734
*Corynebacterium lilium* ATCC 15990
*Corynebacterium melassecola* ATCC 17965
*Corynebacterium efficiens (Corynebacterium thermoaminogenes)* AJ12340 (FERM BP-1539)
*Corynebacterium herculis* ATCC 13868
*Brevibacterium divaricatum (Corynebacterium glutamicum)* ATCC 14020
*Brevibacterium flavum (Corynebacterium glutamicum)* ATCC 13826, ATCC 14067, AJ12418 (FERM BP-2205)
*Brevibacterium immariophilum* ATCC 14068
*Brevibacterium lactofermentum (Corynebacterium glutamicum)* ATCC 13869
*Brevibacterium roseum* ATCC 13825
*Brevibacterium saccharolyticum* ATCC 14066
*Brevibacterium thiogenitalis* ATCC 19240
*Corynebacterium ammoniagenes (Corynebacterium stationis)* ATCC 6871, ATCC 6872
*Brevibacterium album* ATCC 15111
*Brevibacterium cerinum* ATCC 15112
*Microbacterium ammoniaphilum* ATCC 15354

The *Corynebacterium* bacteria can include bacteria that were previously classified into the genus *Brevibacterium*, but are now united into the genus *Corynebacterium* (Int. J. Syst. Bacteriol., 41, 255 (1991)). Moreover, *Corynebacterium stationis* can include bacteria that had previously been classified as *Corynebacterium ammoniagenes*, but are now re-classified into *Corynebacterium stationis* on the basis of nucleotide sequence analysis of 16S rRNA etc. (Int. J. Syst. Evol. Microbiol., 60, 874-879 (2010)).

The *Escherichia* bacteria are not particularly limited, and examples thereof can include bacteria classified into the genus *Escherichia* according to the taxonomy known to those skilled in the field of microbiology. Examples of the *Escherichia* bacteria can include, for example, bacteria described in the work of Neidhardt et al. (Backmann B. J., 1996, Derivations and Genotypes of some mutant derivatives of *Escherichia coli* K-12, pp. 2460-2488, Table 1, In F. D. Neidhardt (ed.), *Escherichia coli* and *Salmonella* Cellular and Molecular Biology/Second Edition, American Society for Microbiology Press, Washington, D.C.). Examples of the *Escherichia* bacteria can include, for example, *Escherichia coli*. Examples of *Escherichia coli* can include, for example, *Escherichia coli* K-12 strains such as W3110 strain (ATCC 27325) and MG1655 strain (ATCC 47076); *Escherichia coli* K5 strain (ATCC 23506); *Escherichia coli* B strains such as BL21 (DE3) strain; and derivative strains thereof.

These strains are available from, for example, the American Type Culture Collection (Address: P.O. Box 1549, Manassas, Va. 20108, United States of America). That is, registration numbers are given to the respective strains, and the strains can be ordered by using these registration numbers (refer to www.atcc.org). The registration numbers of the strains are listed in the catalogue of the American Type Culture Collection. These strains can also be obtained from, for example, the depositories at which the strains were deposited.

The microorganism able to produce a basic amino acid may inherently be able to produce a basic amino acid, or may be modified so that it is able to produce a basic amino acid. The microorganism able to produce a basic amino acid can be obtained by imparting the ability to produce a basic amino acid to such a microorganism as described above, or by enhancing the ability to produce a basic amino acid of such a microorganism as described above.

To impart or enhance the ability to produce a basic amino acid, methods conventionally employed in the breeding of amino acid-producing strains of coryneform bacteria, *Escherichia* bacteria, and so forth (refer to "Amino Acid Fermentation", Gakkai Shuppan Center (Ltd.), 1st Edition, published May 30, 1986, pp. 77-100) can be used. Examples of such methods can include, for example, acquiring an auxotrophic mutant strain, acquiring a basic amino acid analogue-resistant strain, acquiring a metabolic regulation mutant strain, and constructing a recombinant strain in which the activity of a basic amino acid biosynthetic enzyme is enhanced. In the breeding of basic amino acid-producing microorganisms, one of the above-described properties such as auxotrophy, analogue resistance, and metabolic regulation mutation may be imparted alone, or two or three or more of such properties may be imparted in combination. Also, in the breeding of basic amino acid-producing microorganisms, the activity of one of basic amino acid biosynthetic enzymes may be enhanced alone, or the activities of two or three or more of such enzymes may be enhanced in combination. Furthermore, imparting such property(s) as auxotrophy, analogue resistance, and metabolic regulation mutation can be combined with enhancing the activity(s) of biosynthetic enzyme(s).

An auxotrophic mutant strain, analogue-resistant strain, or metabolic regulation mutant strain having a basic amino acid-producing ability can be obtained by subjecting a parental strain or wild-type strain to a usual mutagenesis treatment, and then selecting a strain exhibiting autotrophy, analogue resistance, or a metabolic regulation mutation, and having a basic amino acid-producing ability from the obtained mutant strains. Examples of the usual mutagenesis treatment can include irradiation of X-ray or ultraviolet and a treatment with a mutation agent such as N-methyl-N'-nitro-N-nitrosoguanidine (MNNG), ethyl methanesulfonate (EMS), and methyl methanesulfonate (MMS).

The ability to produce a basic amino acid can be imparted or enhanced by enhancing the activity of a biosynthesis enzyme of an objective basic amino acid. Enzyme activity can be enhanced by, for example, enhancing the expression of a gene encoding the enzyme. Methods for enhancing gene expression are described in WO00/18935, EP1010755A, and so forth. Detailed methods for enhancing enzyme activity are described herein.

Furthermore, the ability to produce a basic amino acid can also be imparted or enhanced by reducing the activity of an enzyme that catalyzes a reaction branching away from the biosynthetic pathway of an objective basic amino acid to generate a compound other than the objective basic amino acid. The "enzyme that catalyzes a reaction branching away from the biosynthetic pathway of an objective basic amino acid to generate a compound other than the objective basic amino acid" can include an enzyme involved in decomposition of the objective amino acid. An enzyme activity can be reduced by, for example, disrupting a gene encoding the enzyme. Detailed methods for reducing an enzyme activity are described herein.

Hereinafter, basic amino acid-producing microorganisms and methods for imparting or enhancing a basic amino acid-producing ability will be specifically exemplified. All of the properties of the basic amino acid-producing microorganisms and modifications for imparting or enhancing a basic amino acid-producing ability may be used independently or in any appropriate combination.

<L-Lysine-Producing Microorganisms>

Examples of methods for imparting or enhancing L-lysine-producing ability can include, for example, a method of modifying a bacterium so that the bacterium has an increased activity or activities of one or more of the L-lysine biosynthesis enzymes. Examples of such enzymes can include, but are not particularly limited to, dihydrodipicolinate synthase (dapA), aspartokinase III (lysC), dihydrodipicolinate reductase (dapB), diaminopimelate decarboxylase (lysA), diaminopimelate dehydrogenase (ddh) (U.S. Pat. No. 6,040,160), phosphoenolpyruvate carboxylase (ppc), aspartate semialdehyde dehydrogenase (asd), aspartate aminotransferase (aspartate transaminase) (aspC), diaminopimelate epimerase (dapF), tetrahydrodipicolinate succinylase (dapD), succinyl diaminopimelate deacylase (dapE), and aspartase (aspA) (EP1253195A). Shown in the parentheses after the names of the enzymes are examples of genes encoding the enzymes (the same shall apply similarly hereinafter). The activity or activities of one or more of, for example, dihydrodipicolinate reductase, diaminopimelate decarboxylase, diaminopimelate dehydrogenase, phosphoenolpyruvate carboxylase, aspartate aminotransferase, diaminopimelate epimerase, aspartate semialdehyde dehydrogenase, tetrahydrodipicolinate succinylase, and succinyl diaminopimelate deacylase. Furthermore, L-lysine-producing bacteria and parental strains used to derive such bacteria can express an increased level of the gene involved in energy efficiency (cyo) (EP1170376A), the gene encoding nicotinamide nucleotide transhydrogenase (pntAB) (U.S. Pat. No. 5,830,716), the ybjE gene (WO2005/073390), or combinations of these. Since aspartokinase III (lysC) is subject to feedback inhibition by L-lysine, a mutant lysC gene encoding an aspartokinase III desensitized to feedback inhibition by L-lysine may be used for enhancing the activity of this enzyme. Examples of the aspartokinase III desensitized to feedback inhibition by L-lysine can include aspartokinase III derived from Escherichia coli and having one or more mutations, such as a mutation for replacing the methionine residue at position 318 with an isoleucine residue; a mutation for replacing the glycine residue at position 323 with an aspartic acid residue; and a mutation for replacing the threonine residue at position 352 with an isoleucine residue (U.S. Pat. Nos. 5,661,012 and 6,040,160). Furthermore, since dihydrodipicolinate synthase (dapA) is subject to feedback inhibition by L-lysine, a mutant dapA gene encoding a dihydrodipicolinate synthase desensitized to feedback inhibition by L-lysine may be used for enhancing the activity of this enzyme. Examples of the dihydrodipicolinate synthase desensitized to feedback inhibition by L-lysine can include dihydrodipicolinate synthase native to Escherichia coli and having a mutation for replacing the histidine residue at position 118 with a tyrosine residue (U.S. Pat. No. 6,040,160).

Examples of methods for imparting or enhancing L-lysine-producing ability also can include, for example, a method of modifying a bacterium so that the bacterium has a reduced activity or activities of one or more enzymes that catalyze a reaction branching away from the biosynthetic pathway of L-lysine to generate a compound other than L-lysine. Examples of such enzymes can include, but are not particularly limited to, homoserine dehydrogenase, lysine decarboxylase (U.S. Pat. No. 5,827,698), and malic enzyme (WO2005/010175).

Furthermore, examples of methods for imparting or enhancing L-lysine-producing ability to or in coryneform bacteria also can include a method of modifying the bacteria so that the activity of a lysine excretion system (lysE) is increased (WO97/23597). The lysE gene of Corynebacterium glutamicum ATCC 13032 corresponds to the sequence complementary to the sequence of the nucleotide numbers 1,329,712 to 1,330,413 in the genome sequence registered as Genbank Accession No. NC_006958 (VERSION NC_006958.1 GI:62388892) in the NCBI database. The LysE protein of Corynebacterium glutamicum ATCC 13032 is registered as GenBank accession No. YP_225551 (YP_225551.1 GI:62390149).

Examples of L-lysine-producing bacteria and parental strains used to derive such bacteria also can include mutant strains having resistance to an L-lysine analogue. L-Lysine analogues inhibit the growth of bacteria such as bacteria of the family Enterobacteriaceae and coryneform bacteria, but this inhibition is fully or partially released when L-lysine is present in the culture medium. Examples of these L-lysine analogues can include, but are not particularly limited to, oxalysine, lysine hydroxamate, S-(2-aminoethyl)-L-cysteine (AEC), γ-methyllysine, and α-chlorocaprolactam. Mutant strains having resistance to these lysine analogues can be obtained by subjecting a bacterium to a conventional artificial mutagenesis treatment.

Specific examples of L-lysine-producing bacteria and parental strains used to derive such bacteria can include E.

coli AJ11442 (FERM BP-1543, NRRL B-12185, U.S. Pat. No. 4,346,170) and *E. coli* VL611. In these strains, aspartokinase is desensitized to feedback inhibition by L-lysine.

Specific examples of L-lysine-producing bacteria and parental strains used to derive such bacteria also can include the *E. coli* WC196 strain. The WC196 strain was bred by imparting AEC resistance to the W3110 strain, which was derived from *E. coli* K-12 (U.S. Pat. No. 5,827,698). The WC196 strain was designated *E. coli* AJ13069 and deposited at the National Institute of Bioscience and Human-Technology, Agency of Industrial Science and Technology (currently, independent administrative agency, National Institute of Technology and Evaluation, International Patent Organism Depositary, #120, 2-5-8 Kazusakamatari, Kisarazu-shi, Chiba-ken, 292-0818, Japan) on Dec. 6, 1994 and assigned an accession number of FERM P-14690. Then, the deposit was converted to an international deposit under the provisions of the Budapest Treaty on Sep. 29, 1995, and assigned an accession number of FERM BP-5252 (U.S. Pat. No. 5,827,698).

Examples of L-lysine-producing bacteria can include *E. coli* WC196ΔcadAΔldc and *E. coli* WC196ΔcadAΔldc/pCABD2 (WO2010/061890). The *E. coli* WC196ΔcadAΔldc is a strain constructed from the WC196 strain by disrupting the cadA and ldcC genes encoding lysine decarboxylase. The WC196ΔcadAΔldc/pCABD2 strain was constructed by introducing the plasmid pCABD2 containing lysine biosynthesis enzyme genes (U.S. Pat. No. 6,040,160) into the WC196ΔcadAΔldc strain. The WC196ΔcadAΔldc strain, designated as AJ110692, was deposited at the independent administrative agency, National Institute of Advanced Industrial Science and Technology, International Patent Organism Depositary (currently, independent administrative agency, National Institute of Technology and Evaluation, International Patent Organism Depositary, #120, 2-5-8 Kazusakamatari, Kisarazu-shi, Chiba-ken, 292-0818, Japan) on Oct. 7, 2008 as an international deposit, and assigned an accession number of FERM BP-11027. The plasmid pCABD2 contains a mutant dapA gene derived from *Escherichia coli* and encoding a dihydrodipicolinate synthase (DDPS) having a mutation for desensitization to feedback inhibition by L-lysine (H118Y), a mutant lysC gene derived from *Escherichia coli* and encoding aspartokinase III having a mutation for desensitization to feedback inhibition by L-lysine (T352I), the dapB gene derived from *Escherichia coli* and encoding dihydrodipicolinate reductase, and the ddh gene derived from *Brevibacterium lactofermentum* and encoding diaminopimelate dehydrogenase.

Examples of L-lysine-producing bacteria also can include *E. coli* AJIK01 (NITE BP-01520). The AJIK01 strain was designated *E. coli* AJ111046, and deposited at the independent administrative agency, National Institute of Technology and Evaluation, International Patent Organism Depositary (#122, 2-5-8 Kazusakamatari, Kisarazu-shi, Chiba-ken, 292-0818, Japan) on Jan. 29, 2013. Then, it was converted to an international deposit under the provisions of the Budapest Treaty on May 15, 2014, and assigned an accession number of NITE BP-01520.

Examples of coryneform bacteria having L-lysine-producing ability can include, for example, the AEC-resistant mutant strains (*Corynebacterium glutamicum* (*Brevibacterium lactofermentum* AJ11082) (NRRL B-11470) strain etc., Japanese Patent Publication (Kokoku) Nos. 56-1914, 56-1915, 57-14157, 57-14158, 57-30474, 58-10075, 59-4993, 61-35840, 62-24074, 62-36673, 5-11958, 7-112437, and 7-112438); mutant strains requiring an amino acid such as L-homoserine for their growth (Japanese Patent Publication Nos. 48-28078 and 56-6499); mutant strains showing resistance to AEC and further requiring an amino acid such as L-leucine, L-homoserine, L-proline, L-serine, L-arginine, L-alanine, and L-valine (U.S. Pat. Nos. 3,708,395 and 3,825,472); mutant strains showing resistance to DL-α-amino-ε-caprolactam, α-amino-lauryllactam, aspartic acid analogue, sulfa drug, quinoid, and N-lauroylleucine; mutant strains showing resistance to an oxaloacetate decarboxylase inhibitor or a respiratory chain enzyme inhibitor (Japanese Patent Laid-open (Kokai) Nos. 50-53588, 50-31093, 52-102498, 53-9394, 53-86089, 55-9783, 55-9759, 56-32995, 56-39778, Japanese Patent Publication Nos. 53-43591 and 53-1833); mutant strains requiring inositol or acetic acid (Japanese Patent Laid-open (Kokai) Nos. 55-9784 and 56-8692); mutant strains that are susceptible to fluoropyruvic acid or a temperature of 34° C. or higher (Japanese Patent Laid-open (Kokai) Nos. 55-9783 and 53-86090); and mutant strains showing resistance to ethylene glycol (U.S. Pat. No. 4,411,997).

<L-Arginine-Producing Microorganisms>

Examples of methods for imparting or enhancing L-arginine-producing ability can include, for example, a method of modifying a bacterium so that the bacterium has an increased activity or activities of one or more of the L-arginine biosynthesis enzymes. Examples of such enzymes can include, but are not particularly limited to, N-acetylglutamate synthase (argA), N-acetylglutamyl phosphate reductase (argC), ornithine acetyl transferase (argJ), N-acetylglutamate kinase (argB), acetylornithine transaminase (argD), acetylornithine deacetylase (argE), ornithine carbamoyl transferase (argF), argininosuccinate synthetase (argG), argininosuccinate lyase (argH), and carbamoyl phosphate synthetase (carAB). As the N-acetylglutamate synthase gene (argA), for example, a gene encoding a mutant N-acetylglutamate synthase desensitized to feedback inhibition by L-arginine by substitution for the amino acid residues corresponding to the positions 15 to 19 of the wild-type enzyme (EP1170361A) can preferably be used.

Specific examples of L-arginine-producing bacteria and parental strains used to derive such bacteria can include, for example, the *E. coli* 237 strain (VKPM B-7925, US2002/058315A1), derivative strains thereof introduced with the argA gene encoding a mutant N-acetyl glutamate synthase (Russian Patent Application No. 2001112869, EP1170361A1), *E. coli* 382 strain derived from the 237 strain and having an improved acetic acid-assimilating ability (VKPM B-7926, EP1170358A1), and *E. coli* 382ilvA+ strain, which is a strain obtained from the 382 strain by introducing the wild-type ilvA gene from *E. coli* K-12 strain thereto. The *E. coli* strain 237 was deposited at the Russian National Collection of Industrial Microorganisms (VKPM, FGUP GosNII Genetika, 1 Dorozhny proezd., 1 Moscow 117545, Russia) on Apr. 10, 2000 under an accession number of VKPM B-7925, and the deposit was converted to an international deposit under the provisions of Budapest Treaty on May 18, 2001. The *E. coli* 382 strain was deposited at the Russian National Collection of Industrial Microorganisms (VKPM, FGUP GosNII Genetika, 1 Dorozhny proezd., 1 Moscow 117545, Russia) on Apr. 10, 2000 under accession number of VKPM B-7926.

Examples of L-arginine-producing bacteria and parental strains used to derive such bacteria also can include strains having resistance to amino acid analogues, and so forth. Examples of such strains can include *E. coli* mutant strains having resistance to α-methylmethionine, p-fluorophenylalanine, D-arginine, arginine hydroxamate, S-(2-aminoethyl)-cysteine, α-methylserine, β-2-thienylalanine, or sulfaguanidine (Japanese Patent Laid-open (Kokai) No. 56-106598).

Examples of L-arginine-producing bacteria and parent strains used to derive such bacteria also can include a coryneform bacteria strain deficient in ArgR, which is an arginine repressor (US2002-0045223A), and a strain in which glutamine synthetase activity is increased (US2005-0014236A).

Examples of L-arginine-producing bacteria and parent strains used to derive such bacteria also can include mutant strains of coryneform bacteria, the mutant strains having resistance to an amino acid analogue or the like. Examples of such strains can include, for example, strains having resistance to 2-thiazolealanine and further exhibiting auxotrophy for L-histidine, L-proline, L-threonine, L-isoleucine, L-methionine, or L-tryptophan (Japanese Patent Laid-open (Kokai) No. 54-44096); strains resistant to ketomalonic acid, fluoromalonic acid, or monofluoroacetic acid (Japanese Patent Laid-open (Kokai) No. 57-18989); strains resistant to argininol (Japanese Patent Publication No. 62-24075); strains resistant to X-guanidine (X represents an aliphatic chain or a derivative thereof, Japanese Patent Laid-open (Kokai) No. 2-186995); and strains resistant to arginine hydroxamate and 6-azauracil (Japanese Patent Laid-open (Kokai) No. 57-150381). Specific examples of coryneform bacteria having L-arginine-producing ability can include the following strains.

*Corynebacterium glutamicum* (*Brevibacterium flavum*) AJ11169 (FERM BP-6892)

*Corynebacterium glutamicum* (*Brevibacterium lactofermentum*) AJ12092 (FERM BP-6906)

*Corynebacterium glutamicum* (*Brevibacterium flavum*) AJ11336 (FERM BP-6893)

*Corynebacterium glutamicum* (*Brevibacterium flavum*) AJ11345 (FERM BP-6894)

*Corynebacterium glutamicum* (*Brevibacterium lactofermentum*) AJ12430 (FERM BP-2228)

<L-Histidine-Producing Microorganisms>

Examples of methods for imparting or enhancing L-histidine-producing ability can include, for example, a method of modifying a bacterium so that the bacterium has an increased activity or activities of one or more of the L-histidine biosynthesis enzymes. Examples of such enzymes can include, but are not particularly limited to, ATP phosphoribosyltransferase (hisG), phosphoribosyl AMP cyclohydrolase (hisI), phosphoribosyl-ATP pyrophosphohydrolase (hisI), phosphoribosylformimino-5-aminoimidazole carboxamide ribotide isomerase (hisA), amidotransferase (hisH), histidinol phosphate aminotransferase (hisC), histidinol phosphatase (hisB), and histidinol dehydrogenase (hisD).

Among these enzymes, the L-histidine biosynthesis enzymes encoded by hisG and hisBHAFI are known to be inhibited by L-histidine. Therefore, the ability to produce L-histidine can be imparted or enhanced by, for example, introducing a mutation for conferring resistance to feedback inhibition into the gene encoding ATP phosphoribosyltransferase (hisG) (Russian Patent Nos. 2,003,677 and 2,119,536).

Specific examples of L-histidine-producing bacteria and parental strains used to derive such bacteria can include, for example, strains belonging to the genus *Escherichia*, such as the *E. coli* 24 strain (VKPM B-5945, RU2003677), *E. coli* NRRL B-12116 to B-12121 (U.S. Pat. No. 4,388,405), *E. coli* H-9342 (FERM BP-6675) and H-9343 (FERM BP-6676, U.S. Pat. No. 6,344,347), *E. coli* H-9341 (FERM BP-6674, EP1085087), *E. coli* AI80/pFM201 (U.S. Pat. No. 6,258,554), *E. coli* FERM P-5038 and FERM P-5048, which have been introduced with a vector carrying a DNA encoding an L-histidine-biosynthesis enzyme (Japanese Patent Laid-open (Kokai) No. 56-005099), *E. coli* strains introduced with a gene for amino acid transport (EP1016710A), and *E. coli* 80 strain, which has been imparted with resistance to sulfaguanidine, DL-1,2,4-triazole-3-alanine, and streptomycin (VKPM B-7270, Russian Patent No. 2119536).

Furthermore, examples of methods for imparting or enhancing a basic amino acid-producing ability also can include, for example, a method of modifying a bacterium so that the bacterium has an increased activity or activities of one or more of the proteins involved in glycometabolism and of proteins involved in the energy metabolism.

Examples of the proteins involved in the glycometabolism can include proteins involved in uptake of saccharides and the glycolysis system enzymes. Examples of genes encoding a protein involved in the glycometabolism can include glucose-6-phosphate isomerase gene (pgi, WO01/02542), pyruvate carboxylase gene (pyc, WO99/18228, EP1092776A), phosphoglucomutase gene (pgm, WO03/04598), fructose bisphosphate aldolase gene (pfkB, fbp, WO03/04664), transaldolase gene (talB, WO03/008611), fumarase gene (fum, WO01/02545), non-PTS sucrose uptake gene (csc, EP1149911A), and sucrose assimilation gene (scrAB operon, U.S. Pat. No. 7,179,623).

Examples of genes encoding the proteins involved in the energy metabolism can include the transhydrogenase gene (pntAB, U.S. Pat. No. 5,830,716) and cytochrome bo-type oxidase gene (cyoB, EP1070376A).

The genes and proteins used for breeding basic amino acid-producing microorganisms may have, for example, known nucleotide sequences and amino acid sequences of the genes and proteins exemplified above (hereinafter, also referred to simply as "known nucleotide and amino acid sequences"), respectively. The expression "a gene or protein has a nucleotide or amino acid sequence" can include when the gene or protein includes the nucleotide or amino acid sequence plus other inconsequential sequences, and when the gene or protein includes only the nucleotide or amino acid sequence. Also, the genes and proteins used for breeding basic amino acid-producing microorganisms may be conservative variants of genes and proteins having known nucleotide and amino acid sequences, respectively. The term "conservative variant" can refer to a variant that maintains the original function thereof. Examples of the conservative variants can include, for example, homologues and artificially modified versions of genes and proteins having known nucleotide and amino acid sequences.

The expression "the original function is maintained" can mean that a variant of gene or protein has a function (such as activity or property) corresponding to the function (such as activity or property) of the original gene or protein. The expression "the original function is maintained" used for a gene can mean that a variant of the gene encodes a protein that maintains the original function. For example, the expression "the original function is maintained" used for dihydrodipicolinate reductase gene can mean that a variant of the gene encodes a protein having dihydrodipicolinate reductase activity. Furthermore, the expression "the original function is maintained" used for dihydrodipicolinate reductase can mean that a variant of the protein has dihydrodipicolinate reductase activity.

Hereinafter, examples of the conservative variants will be described.

Homologues of the genes and proteins used for breeding basic amino acid-producing microorganisms can be easily obtained from public databases by, for example, BLAST search or FASTA search using any known nucleotide and amino acid sequences as a query sequence. Furthermore, homologues of the genes used for breeding basic amino acid-producing microorganisms can be obtained by, for example, PCR using a chromosome of organisms such as coryneform bacteria as the template, and oligonucleotides prepared on the basis of any of known nucleotide sequences as primers.

The genes used for breeding basic amino acid-producing microorganisms each may be a gene encoding a protein having any known amino acid sequences, but which can include substitution, deletion, insertion, or addition of one or several amino acid residues at one or several positions, so long as the original function is maintained. For example, the N-terminus and/or the C-terminus of the encoded protein may be elongated or shortened. Although the number meant by the term "one or several" mentioned above may differ depending on the positions of amino acid residues in the three-dimensional structure of the protein or the types of amino acid residues, specifically, it can be, for example, 1 to 50, 1 to 40, 1 to 30, 1 to 20, 1 to 10, 1 to 5, or 1 to 3.

The aforementioned substitution, deletion, insertion, or addition of one or several amino acid residues can be a conservative mutation that maintains the normal function of the protein. Typical examples of the conservative mutation are conservative substitutions. The conservative substitution can be a mutation wherein substitution takes place mutually among Phe, Trp, and Tyr, if the substitution site is an aromatic amino acid; among Leu, Ile, and Val, if it is a hydrophobic amino acid; between Gln and Asn, if it is a polar amino acid; among Lys, Arg, and His, if it is a basic amino acid; between Asp and Glu, if it is an acidic amino acid; and between Ser and Thr, if it is an amino acid having a hydroxyl group. Examples of substitutions considered as conservative substitutions can include, specifically, substitution of Ser or Thr for Ala, substitution of Gln, His, or Lys for Arg, substitution of Glu, Gln, Lys, His, or Asp for Asn, substitution of Asn, Glu, or Gln for Asp, substitution of Ser or Ala for Cys, substitution of Asn, Glu, Lys, His, Asp, or Arg for Gln, substitution of Gly, Asn, Gln, Lys, or Asp for Glu, substitution of Pro for Gly, substitution of Asn, Lys, Gln, Arg, or Tyr for His, substitution of Leu, Met, Val, or Phe for Ile, substitution of Ile, Met, Val, or Phe for Leu, substitution of Asn, Glu, Gln, His, or Arg for Lys, substitution of Ile, Leu, Val, or Phe for Met, substitution of Trp, Tyr, Met, Ile, or Leu for Phe, substitution of Thr or Ala for Ser, substitution of Ser or Ala for Thr, substitution of Phe or Tyr for Trp, substitution of His, Phe, or Trp for Tyr, and substitution of Met, Ile, or Leu for Val. Furthermore, such substitution, deletion, insertion, addition, inversion, or the like of amino acid residues as mentioned above includes a naturally occurring mutation due to an individual difference, or a difference of species of the organism from which the gene is derived (mutant or variant).

The genes used for breeding basic amino acid-producing microorganisms each may be a gene encoding a protein having an amino acid sequence showing a homology of, for example, 50% or more, 65% or more, 80% or more, 90% or more, 95% or more, 97% or more, or 99% or more, to the total amino acid sequence of any known amino acid sequences, so long as the original function is maintained. In this description, "homology" can mean "identity".

The genes used for breeding basic amino acid-producing microorganisms each may also be a DNA that is able to hybridize under stringent conditions with a probe that can be prepared from any known nucleotide sequences, such as a sequence complementary to a partial or entire sequence of any known nucleotide sequences, so long as the original function is maintained. The term "stringent conditions" can refer to conditions under which a so-called specific hybrid is formed, and a non-specific hybrid is not formed. Examples of the stringent conditions can include those under which highly homologous DNAs hybridize to each other, for example, DNAs not less than 50%, 65%, 80%, 90% homologous, 95%, 97%, or 99% homologous, hybridize to each other, and DNAs less homologous than the above do not hybridize to each other, or conditions of washing of typical Southern hybridization, i.e., conditions of washing once, 2 or 3 times, at a salt concentration and temperature corresponding to 1×SSC, 0.1% SDS at 60° C.; or 0.1×SSC, 0.1% SDS at 60° C., or 0.1×SSC, 0.1% SDS at 68° C.

The probe used for the aforementioned hybridization may be a part of a sequence that is complementary to the gene as described above. Such a probe can be prepared by PCR using oligonucleotides prepared on the basis of any known nucleotide sequences as primers and a DNA fragment containing any the aforementioned genes as a template. As the probe, for example, a DNA fragment having a length of about 300 bp can be used. When a DNA fragment having a length of about 300 bp is used as the probe, the washing conditions of the hybridization may be, for example, 50° C., 2×SSC and 0.1% SDS.

Furthermore, since the degeneracy of codons differs depending on the host, any codons in the genes used for breeding basic amino acid-producing microorganisms may be replaced with respective equivalent codons.

The percentage of the sequence identity between two sequences can be determined by, for example, using a mathematical algorithm. Non-limiting examples of such a mathematical algorithm can include the algorithm of Myers and Miller (1988) CABIOS 4:11-17, the local homology algorithm of Smith et al (1981) Adv. Appl. Math. 2:482, the homology alignment algorithm of Needleman and Wunsch (1970) J. Mol. Biol. 48:443-453, the method for searching homology of Pearson and Lipman (1988) Proc. Natl. Acad. Sci. 85:2444-2448, and a modified version of the algorithm of Karlin and Altschul (1990) Proc. Natl. Acad. Sci. USA 87:2264, such as that described in Karlin and Altschul (1993) Proc. Natl. Acad. Sci. USA 90:5873-5877.

By using a program based on such a mathematical algorithm, sequence comparison (i.e. alignment) for determining the sequence identity can be performed. The program can be appropriately executed by a computer. Examples of such a program can include, but are not limited to, CLUSTAL of PC/Gene program (available from Intelligenetics, Mountain View, Calif.), ALIGN program (Version 2.0), and GAP, BESTFIT, BLAST, FASTA, and TFASTA of Wisconsin Genetics Software Package, Version 8 (available from Genetics Computer Group (GCG), 575 Science Drive, Madison, Wis., USA). Alignment using these programs can be performed by using, for example, initial parameters. The CLUSTAL program is well described in Higgins et al. (1988) Gene 73:237-244 (1988), Higgins et al. (1989) CABIOS 5:151-153, Corpet et al. (1988) Nucleic Acids Res. 16:10881-90, Huang et al. (1992) CABIOS 8:155-65, and Pearson et al. (1994) Meth. Mol. Biol. 24:307-331.

In order to obtain a nucleotide sequence homologous to a target nucleotide sequence, in particular, for example, BLAST nucleotide search can be performed by using BLASTN program with score of 100 and word length of 12. In order to obtain an amino acid sequence homologous to a target protein, in particular, for example, BLAST protein search can be performed by using BLASTX program with score of 50 and word length of 3. See www.ncbi.nlm.nih.gov for BLAST nucleotide search and BLAST protein search. In addition, Gapped BLAST (BLAST 2.0) can be used in order to obtain an alignment including gap(s) for the purpose of comparison. In addition, PSI-BLAST (BLAST 2.0) can be used in order to perform repetitive search for detecting distant relationships between sequences. See Altschul et al. (1997) Nucleic Acids Res. 25:3389 for Gapped BLAST and PSI-BLAST. When using BLAST, Gapped BLAST, or PSI-BLAST, initial parameters of each program (e.g. BLASTN for nucleotide sequences, and BLASTX for amino acid sequences) can be used. Alignment can also be manually performed.

The sequence identity between two sequences is calculated as the ratio of residues matching in the two sequences when aligning the two sequences so as to fit maximally with each other.

<1-2> Methods for Increasing Activity of Protein

Hereinafter, methods for increasing the activity of a protein will be explained.

The expression "the activity of a protein is increased" can mean that the activity of the protein per cell is increased as compared with that of a non-modified strain, such as a wild-type strain or parent strain. The term "non-modified strain" can refer to a control strain that has not been modified so that the activity of an objective protein is increased. Examples of the non-modified strain can include a wild-type strain and parent strain. The state that "the activity of a protein is increased" may also be expressed as "the activity of a protein is enhanced". Specifically, the expression "the activity of a protein is increased" can mean that the number of molecules of the protein per cell is increased, and/or the function of each molecule of the protein is increased as compared with those of a non-modified strain. That is, the term "activity" in the expression "the activity of a protein is increased" is not limited to the catalytic activity of the protein, but may also mean the transcription amount of a gene (i.e. the amount of mRNA) encoding the protein, or the translation amount of the gene (i.e. the amount of the protein). Furthermore, the expression "the activity of a protein is increased" can include not only when the activity of an objective protein is increased in a strain inherently having the activity of the objective protein, but also when the activity of an objective protein is imparted to a strain not inherently having the activity of the objective protein. Furthermore, so long as the activity of the protein is eventually increased, the activity of an objective protein inherently present in a host may be attenuated and/or eliminated, and then an appropriate type of the objective protein may be imparted to the host.

The degree of the increase in the activity of a protein is not particularly limited, so long as the activity of the protein is increased as compared with a non-modified strain. The activity of the protein may be increased to, for example, 1.5 times or more, 2 times or more, or 3 times or more of that of a non-modified strain. Furthermore, when the non-modified strain does not have the activity of the objective protein, it is sufficient that the protein is produced as a result of introduction of the gene encoding the protein, and for example, the protein may be produced to such an extent that the activity thereof can be measured.

The modification for increasing the activity of a protein is attained by, for example, increasing the expression of a gene encoding the protein. The expression "the expression of a gene is increased" can mean that the expression amount of the gene per cell is increased as compared with that of a non-modified strain such as a wild-type strain and parent strain. Specifically, the expression "the expression of a gene is increased" may mean that the transcription amount of the gene (i.e. the amount of mRNA) is increased, and/or the translation amount of the gene (i.e. the amount of the protein expressed from the gene) is increased. The expression "the expression of a gene is increased" may also be referred to as "the expression of a gene is enhanced". The expression of a gene may be increased to, for example, 1.5 times or more, 2 times or more, or 3 times or more of that of a non-modified strain. Furthermore, the state that "the expression of a gene is increased" can include not only a when the expression amount of an objective gene is increased in a strain that inherently expresses the objective gene, but also when the gene is introduced into a strain that does not inherently express the objective gene, and expressed therein. That is, the phrase "the expression of a gene is increased" may also mean, for example, that an objective gene is introduced into a strain that does not possess the gene, and is expressed therein.

The expression of a gene can be increased by, for example, increasing the copy number of the gene.

The copy number of a gene can be increased by introducing the gene into the chromosome of a host. A gene can be introduced into a chromosome by, for example, using homologous recombination (Miller, J. H., Experiments in Molecular Genetics, 1972, Cold Spring Harbor Laboratory). Examples of the gene transfer method utilizing homologous recombination can include, for example, a method of using a linear DNA such as Red-driven integration (Datsenko, K. A., and Wanner, B. L., Proc. Natl. Acad. Sci. USA, 97:6640-6645 (2000)), a method of using a plasmid containing a temperature sensitive replication origin, a method of using a plasmid capable of conjugative transfer, a method of using a suicide vector not having a replication origin that functions in a host, and a transduction method using a phage. Only one copy, or two or more copies of a gene may be introduced. For example, by performing homologous recombination using a sequence which is present in multiple copies on a chromosome as a target, multiple copies of a gene can be introduced into the chromosome. Examples of such a sequence which is present in multiple copies on a chromosome can include repetitive DNAs, and inverted repeats located at the both ends of a transposon. Alternatively, homologous recombination may be performed by using an appropriate sequence on a chromosome such as a gene unnecessary for production of an objective substance as a target. Furthermore, a gene can also be randomly introduced into a chromosome by using a transposon or Mini-Mu (Japanese Patent Laid-open (Kokai) No. 2-109985, U.S. Pat. No. 5,882,888, EP805867B1).

Introduction of a target gene into a chromosome can be confirmed by Southern hybridization using a probe having a sequence complementary to the whole gene or a part thereof, PCR using primers prepared on the basis of the sequence of the gene, or the like.

Furthermore, the copy number of a gene can also be increased by introducing a vector containing the gene into a host. For example, the copy number of a target gene can be increased by ligating a DNA fragment containing the target gene with a vector that functions in a host to construct an expression vector of the gene, and transforming the host with the expression vector. The DNA fragment containing the target gene can be obtained by, for example, PCR using the genomic DNA of a microorganism having the target gene as the template. As the vector, a vector autonomously replicable in the cell of the host can be used. The vector can be a multi-copy vector. Furthermore, the vector can have a marker such as an antibiotic resistance gene for selection of transformant. Furthermore, the vector may have a promoter and/or terminator for expressing the introduced gene. The vector may be, for example, a vector derived from a bacterial plasmid, a vector derived from a yeast plasmid, a vector derived from a bacteriophage, cosmid, phagemid, or the like. Specific examples of vector autonomously replicable in Enterobacteriaceae bacteria such as *Escherichia coli* can include, for example, pUC19, pUC18, pHSG299, pHSG399, pHSG398, pBR322, pSTV29 (all of these are available from Takara Bio), pACYC184, pMW219 (NIPPON GENE), pTrc99A (Pharmacia), pPROK series vectors (Clontech), pKK233-2 (Clontech), pET series vectors (Novagen), pQE series vectors (QIAGEN), pCold TF DNA (Takara Bio), pACYC series vectors, and the broad host spectrum vector RSF1010. Specific examples of vector autonomously replicable in coryneform bacteria can include, for example, pHM1519 (Agric. Biol. Chem., 48, 2901-2903 (1984)); pAM330 (Agric. Biol. Chem., 48, 2901-2903 (1984)); plasmids obtained by improving these and having a drug resistance gene; plasmid pCRY30 (Japanese Patent Laid-open (Kokai) No. 3-210184); plasmids pCRY21, pCRY2KE, pCRY2KX, pCRY31, pCRY3KE, and pCRY3KX (Japanese Patent Laid-open (Kokai) No. 2-72876 and U.S. Pat. No. 5,185,262); plasmids pCRY2 and pCRY3 (Japanese Patent Laid-open (Kokai) No. 1-191686); pAJ655, pAJ611, and pAJ1844 (Japanese Patent Laid-open (Kokai) No. 58-192900); pCG1 (Japanese Patent Laid-open (Kokai) No. 57-134500); pCG2 (Japanese Patent Laid-open (Kokai) No. 58-35197); pCG4 and pCG11 (Japanese Patent Laid-open (Kokai) No. 57-183799); pVK7 (Japanese Patent Laid-open (Kokai) No. 10-215883); and pVC7 (Japanese Patent Laid-open (Kokai) No. 9-070291).

When a gene is introduced, it is sufficient that the gene is able to be expressed by the bacterium as described herein. Specifically, it is sufficient that the gene is introduced so that it is expressed under the control of a promoter sequence that functions in the bacterium as described herein. The promoter may be a promoter derived from the host, or a heterogenous promoter. The promoter may be the native promoter of the gene to be introduced, or a promoter of another gene. As the promoter, for example, such a stronger promoter as described herein may also be used.

A terminator for termination of gene transcription may be located downstream of the gene. The terminator is not particularly limited so long as it functions in the bacterium as described herein. The terminator may be a terminator derived from or native to the host, or a heterogenous terminator. The terminator may be the native terminator of the gene to be introduced, or a terminator of another gene. Specific examples of the terminator can include, for example, T7 terminator, T4 terminator, fd phage terminator, tet terminator, and trpA terminator.

Vectors, promoters, and terminators available in various microorganisms can be used, and are disclosed in detail in "Fundamental Microbiology Vol. 8, Genetic Engineering, KYORITSU SHUPPAN CO., LTD, 1987".

Furthermore, when two or more of genes are introduced, it is sufficient that each of the genes are able to be expressed by the bacterium as described herein. For example, all the genes may be present in a single expression vector or a chromosome. Furthermore, the genes may be separately present on two or more expression vectors, or separately present on a single or two or more expression vectors and a chromosome. An operon made up of two or more genes may also be introduced. When "introducing two or more genes", for example, the respective genes encoding two or more kinds of enzymes, the respective genes encoding two or more subunits making up a single enzyme, and a combination of these, may be used.

The gene to be introduced is not particularly limited so long as it encodes a protein that functions in the host. The gene to be introduced may be a gene derived from or native to the host, or may be a heterogenous gene. The gene to be introduced can be obtained by, for example, PCR using primers designed on the basis of the nucleotide sequence of the gene, and using the genomic DNA of an organism having the gene, a plasmid carrying the gene, or the like as a template. The gene to be introduced may also be totally synthesized, for example, on the basis of the nucleotide sequence of the gene (Gene, 60(1), 115-127 (1987)). The obtained gene can be used as it is, or after being modified as required.

Incidentally, when a protein functions as a complex made up of a plurality of subunits, some or all of the subunits may be modified, so long as the activity of the protein is eventually increased. That is, for example, when the activity of a protein is increased by increasing the expression of a gene, the expression of some or all of the genes that encode the subunits may be enhanced. It is usually preferable to enhance the expression of all of the genes encoding the subunits. Furthermore, the subunits that make up the complex may be derived from or native to a single kind of organism or two or more kinds of organisms, so long as the complex has a function of the objective protein. That is, for example, genes of the same organism encoding a plurality of subunits may be introduced into a host, or genes of different organisms encoding a plurality of subunits may be introduced into a host.

Furthermore, the expression of a gene can be increased by improving the transcription efficiency of the gene. In addition, the expression of a gene can also be increased by improving the translation efficiency of the gene. The transcription efficiency of the gene and the translation efficiency of the gene can be improved by, for example, modifying an expression control sequence of the gene. The term "expression control sequence" collectively can refer to sites that affect the expression of a gene. Examples of the expression control sequence can include, for example, promoter, Shine-Dalgarno (SD) sequence (also referred to as ribosome binding site (RBS)), and spacer region between RBS and the start codon. Expression control sequences can be identified by using a promoter search vector or gene analysis software such as GENETYX. These expression control sequences can be modified by, for example, a method of using a temperature sensitive vector, or the Red driven integration method (WO2005/010175).

The transcription efficiency of a gene can be improved by, for example, replacing the promoter of the gene on a chromosome with a stronger promoter. The term "stronger promoter" can refer to a promoter providing improved transcription of a gene compared with an inherent wild-type promoter of the gene. Examples of stronger promoters can include, for example, the known high expression promoters such as T7 promoter, trp promoter, lac promoter, thr promoter, tac promoter, trc promoter, tet promoter, araBAD promoter, rpoH promoter, msrA promoter, Pm1 promoter (derived from the genus *Bifidobacterium*), PR promoter, and PL promoter. Examples of stronger promoters usable in coryneform bacteria can include the artificially modified P54-6 promoter (Appl. Microbiol. Biotechnol., 53, 674-679 (2000)), pta, aceA, aceB, adh, and amyE promoters inducible in coryneform bacteria with acetic acid, ethanol, pyruvic acid, or the like, cspB, SOD, and tuf (EF-Tu) promoters, which are potent promoters capable of providing a large expression amount in coryneform bacteria (Journal of Biotechnology, 104 (2003) 311-323; Appl. Environ. Microbiol., 2005 December; 71 (12):8587-96), as well as lac promoter, tac promoter, and trc promoter. Furthermore, as the stronger promoter, a highly-active type of an existing promoter may also be obtained by using various reporter genes. For example, by making the −35 and −10 regions in a promoter region closer to the consensus sequence, the activity of the promoter can be enhanced (WO00/18935). Examples of highly active-type promoter can include various tac-like promoters (Katashkina J I et al., Russian Federation Patent Application No. 2006134574) and pnlp8 promoter (WO2010/027045). Methods for evaluating the strength of promoters and examples of strong promoters are described in the paper of Goldstein et al. (Prokaryotic Promoters in Biotechnology, Biotechnol. Annu. Rev., 1, 105-128 (1995)), and so forth.

The translation efficiency of a gene can be improved by, for example, replacing the Shine-Dalgarno (SD) sequence (also referred to as ribosome binding site (RBS)) for the gene on a chromosome with a stronger SD sequence. The "stronger SD sequence" can mean a SD sequence that provides an improved translation of mRNA compared with the inherent wild-type SD sequence of the gene. Examples of stronger SD sequences can include, for example, RBS of the gene 10 derived from phage T7 (Olins P. O. et al, Gene, 1988, 73, 227-235). Furthermore, it is known that substitution, insertion, or deletion of several nucleotides in a spacer region between RBS and the start codon, especially in a sequence immediately upstream of the start codon (5'-UTR), significantly affects the stability and translation efficiency of mRNA, and hence, the translation efficiency of a gene can also be improved by modifying them.

The translation efficiency of a gene can also be improved by, for example, modifying codons. In *Escherichia coli* etc., a clear codon bias exists among the 61 amino acid codons found within the population of mRNA molecules, and the level of cognate tRNA appears directly proportional to the frequency of codon usage (Kane, J. F., Curr. Opin. Biotechnol., 6 (5), 494-500 (1995)). That is, if there is a large amount of mRNA containing an excess number of rare codons, a translational problem may arise. According to the recent research, it is suggested that clusters of AGG/AGA, CUA, AUA, CGA, or CCC codons may especially reduce both the quantity and quality of a synthesized protein. Such a problem occurs especially at the time of expression of a heterologous gene. Therefore, in the case of heterogenous expression of a gene or the like, the translation efficiency of the gene can be improved by replacing a rare codon present in the gene with a more frequently used synonymous codon. That is, the gene to be introduced may be modified, for example, so as to contain optimal codons according to the frequencies of codons observed in the chosen host. Codons can be replaced by, for example, the site-specific mutation method for introducing an objective mutation into an objective site of DNA. Examples of the site-specific mutation method can include the method utilizing PCR (Higuchi, R., 61, in PCR Technology, Erlich, H. A. Eds., Stockton Press (1989); Carter, P., Meth. in Enzymol., 154, 382 (1987)), and the method utilizing phage (Kramer, W. and Frits, H. J., Meth. in Enzymol., 154, 350 (1987); Kunkel, T. A. et al., Meth. in Enzymol., 154, 367 (1987)). Alternatively, a gene fragment in which objective codons are replaced may be totally synthesized. Frequencies of codons in various organisms are disclosed in the "Codon Usage Database" (www.kazusa.or.jp/codon; Nakamura, Y. et al, Nucl. Acids Res., 28, 292 (2000)).

Furthermore, the expression of a gene can also be increased by amplifying a regulator that increases the expression of the gene, or deleting or attenuating a regulator that reduces the expression of the gene.

Such methods for increasing the gene expression as mentioned above may be used independently or in any combination.

Furthermore, the modification that increases the activity of a protein can also be attained by, for example, enhancing the specific activity of the enzyme. Enhancement of the specific activity also can include a reduction and elimination of feedback inhibition. A protein having an enhanced specific activity can be obtained by, for example, searching various organisms. Furthermore, a highly-active type of an existing protein may also be obtained by introducing a mutation into the existing protein. The mutation to be introduced may be, for example, substitution, deletion, insertion, or addition of one or several amino acid residues at one or several position of the protein. The mutation can be introduced by, for example, such a site-specific mutation method as mentioned above. The mutation may also be introduced by, for example, a mutagenesis treatment. Examples of the mutagenesis treatment can include irradiation of X-ray, irradiation of ultraviolet, and a treatment with a mutation agent such as N-methyl-N'-nitro-N-nitrosoguanidine (MNNG), ethyl methanesulfonate (EMS), and methyl methanesulfonate (MMS). Furthermore, a random mutation may be induced by directly treating DNA in vitro with hydroxylamine. Enhancement of the specific activity may be independently used, or may be used in any combination with such methods for enhancing gene expression as mentioned above.

The method for the transformation is not particularly limited, and conventionally known methods can be used. There can be used, for example, a method of treating recipient cells with calcium chloride so as to increase the permeability thereof for DNA, which has been reported for the *Escherichia coli* K-12 strain (Mandel, M. and Higa, A., J. Mol. Biol., 1970, 53, 159-162), and a method of preparing competent cells from cells which are in the growth phase, followed by transformation with DNA, which has been reported for *Bacillus subtilis* (Duncan, C. H., Wilson, G. A. and Young, F. E., Gene, 1977, 1:153-167). Alternatively, there can also be used a method of making DNA-recipient cells into protoplasts or spheroplasts, which can easily take up recombinant DNA, followed by introducing a recombinant DNA into the DNA-recipient cells, which is known to be applicable to *Bacillus subtilis*, actinomycetes, and yeasts (Chang, S. and Choen, S. N., 1979, Mol. Gen. Genet., 168:111-115; Bibb, M. J., Ward, J. M. and Hopwood, O. A., 1978, Nature, 274:398-400; Hinnen, A., Hicks, J. B. and Fink, G. R., 1978, Proc. Natl. Acad. Sci. USA, 75:1929-1933). Furthermore, the electric pulse method reported for coryneform bacteria (Japanese Patent Laid-open (Kokai) No. 2-207791) can also be used.

An increase in the activity of a protein can be confirmed by measuring the activity of the protein.

An increase in the activity of a protein can also be confirmed by confirming an increase in the expression of a gene encoding the protein. An increase in the expression of a gene can be confirmed by confirming an increase in the transcription amount of the gene, or by confirming an increase in the amount of a protein expressed from the gene.

An increase of the transcription amount of a gene can be confirmed by comparing the amount of mRNA transcribed from the gene with that of a non-modified strain such as a wild-type strain or parent strain. Examples of the method for evaluating the amount of mRNA can include Northern hybridization, RT-PCR, and so forth (Sambrook, J., et al., Molecular Cloning A Laboratory Manual/Third Edition, Cold Spring Harbor Laboratory Press, Cold Spring Harbor (USA), 2001). The amount of mRNA may be increased to, for example, 1.5 times or more, 2 times or more, or 3 times or more of that of a non-modified strain.

An increase in the amount of a protein can be confirmed by Western blotting using antibodies (Molecular Cloning, Cold Spring Harbor Laboratory Press, Cold Spring Harbor (USA), 2001). The amount of the protein may be increased to, for example, 1.5 times or more, 2 times or more, or 3 times or more of that of a non-modified strain.

The aforementioned methods for increasing the activity of a protein can be used for enhancement of the activities of any proteins, such as basic amino acid biosynthesis enzymes and lysine excretion system, and enhancement of the expression of any genes, such as genes encoding basic amino acid biosynthesis enzymes and lysine excretion system.

<1-3> Method for Reducing Activity of Protein

Hereinafter, the methods for reducing the activity of a protein will be described.

The expression "the activity of a protein is reduced" can mean that the activity of the protein per cell is reduced as compared with that of a non-modified strain, such as a wild-type strain or parent strain. The term "non-modified strain" can refer to a control strain that has not been modified so that the activity of an objective protein is reduced. Examples of the non-modified strain can include a wild-type strain and parent strain. The expression "the activity of a protein is reduced" also can include when the activity of the protein has completely disappeared. Specifically, the expression "the activity of a protein is reduced" can mean that the number of molecules of the protein per cell is reduced, and/or the function of each molecule of the protein is reduced as compared with those of a non-modified strain. That is, the term "activity" in the expression "the activity of a protein is reduced" is not limited to the catalytic activity of the protein, but may also mean the transcription amount of a gene (i.e. the amount of mRNA) encoding the protein or the translation amount of the protein (i.e. the amount of the protein). The expression "the number of molecules of the protein per cell is reduced" also can include when the protein does not exist at all. The expression "the function of each molecule of the protein is reduced" also can include when the function of each protein molecule has completely disappeared. The degree of the reduction in the activity of a protein is not particularly limited, so long as the activity is reduced as compared with that of a non-modified strain. The activity of a protein may be reduced to, for example, 50% or less, 20% or less, 10% or less, 5% or less, or 0% of that of a non-modified strain.

The modification for reducing the activity of a protein can be attained by, for example, reducing the expression of a gene encoding the protein. The expression "the expression of a gene is reduced" can mean that the expression of the gene per cell is reduced as compared with that of a non-modified strain such as a wild-type strain and parent strain. The expression "the expression of a gene is reduced" may specifically mean that the transcription amount of the gene (i.e. the amount of mRNA) is reduced, and/or the translation amount of the gene (i.e. the amount of the protein expressed from the gene) is reduced. The expression "the expression of a gene is reduced" also can include when the gene is not expressed at all. The expression "the expression of a gene is reduced" can also be referred to as "the expression of a gene is attenuated". The expression of a gene may be reduced to, for example, 50% or less, 20% or less, 10% or less, 5% or less, or 0% of that of a non-modified strain.

The reduction in gene expression may be due to, for example, a reduction in the transcription efficiency, a reduction in the translation efficiency, or a combination of them. The expression of a gene can be reduced by modifying an expression control sequence of the gene such as promoter, Shine-Dalgarno (SD) sequence (also referred to as ribosome-binding site (RBS)), and spacer region between RBS and the start codon of the gene. When an expression control sequence is modified, one or more nucleotides, two or more nucleotides, or three or more nucleotides, of the expression control sequence can be modified. Furthermore, a part or the whole of an expression control sequence may be deleted. The expression of a gene can also be reduced by, for example, manipulating a factor responsible for expression control. Examples of the factor responsible for expression control can include low molecules responsible for transcription or translation control (inducers, inhibitors, etc.), proteins responsible for transcription or translation control (transcription factors etc.), nucleic acids responsible for transcription or translation control (siRNA etc.), and so forth. Furthermore, the expression of a gene can also be reduced by, for example, introducing a mutation that reduces the expression of the gene into the coding region of the gene. For example, the expression of a gene can be reduced by replacing a codon in the coding region of the gene with a synonymous codon used less frequently in a host. Furthermore, for example, the gene expression may be reduced due to disruption of a gene as described later.

The modification for reducing the activity of a protein can also be attained by, for example, disrupting a gene encoding the protein. The expression "a gene is disrupted" can mean that a gene is modified so that a protein that can normally function is not produced. The expression "a protein that normally functions is not produced" can include when the protein is not produced at all from the gene, and when the protein of which the function (such as activity or property) per molecule is reduced or eliminated is produced from the gene.

Disruption of a gene can be attained by, for example, deleting a part or the entire coding region of the gene on a chromosome. Furthermore, the entire gene including sequences upstream and downstream from the gene on a chromosome may be deleted. The region to be deleted may be any region such as an N-terminus region, an internal region, or a C-terminus region, so long as the activity of the protein can be reduced. Deletion of a longer region can usually more surely inactivate the gene. Furthermore, reading frames of the sequences upstream and downstream from the region that are deleted can be not the same.

Disruption of a gene can also be attained by, for example, introducing a mutation for an amino acid substitution (missense mutation), a stop codon (nonsense mutation), a frame shift mutation which adds or deletes one or two nucleotide residues, or the like into the coding region of the gene on a chromosome (Journal of Biological Chemistry, 272:8611-8617 (1997); Proceedings of the National Academy of Sciences, USA, 95 5511-5515 (1998); Journal of Biological Chemistry, 26 116, 20833-20839 (1991)).

Disruption of a gene can also be attained by, for example, inserting another sequence into a coding region of the gene on a chromosome. The insertion site may be in any region of the gene, and insertion of a longer region can usually more surely inactivate the gene. Reading frames of the sequences upstream and downstream from the insertion site can be not the same. The other sequence is not particularly limited so long as a sequence that reduces or eliminates the activity of the encoded protein is chosen, and examples thereof can include, for example, a marker gene such as antibiotic resistance genes, and a gene useful for production of an objective substance.

Such modification of a gene on a chromosome as described above can be attained by, for example, preparing a deficient-type gene modified so that it is unable to produce a protein that normally functions, and transforming a host with a recombinant DNA containing the deficient-type gene to cause homologous recombination between the deficient-type gene and the wild-type gene on a chromosome and thereby substitute the deficient-type gene for the wild-type gene on the chromosome. In this procedure, if a marker gene selected according to the characteristics of the host such as auxotrophy is included in the recombinant DNA, the operation becomes easier. Examples of the deficient-type gene can include a gene in which all or a part of the gene is deleted, a gene that includes a missense mutation, a gene that includes a nonsense mutation, a gene that includes a frame shift mutation, and a gene that includes insertion of a transposon or marker gene. The protein encoded by the deficient-type gene has a conformation different from that of the wild-type protein, even if it is produced, and thus the function thereof can be reduced or eliminated. Such gene disruption based on gene substitution utilizing homologous recombination has already been established, and there are methods of using a linear DNA such as a method called "Red driven integration" (Datsenko, K. A., and Wanner, B. L., Proc. Natl. Acad. Sci. USA, 97:6640-6645 (2000)), and a method utilizing the Red driven integration in combination with an excision system derived from λ phage (Cho, E. H., Gumport, R. I., Gardner, J. F., J. Bacteriol., 184:5200-5203 (2002)) (refer to WO2005/010175), a method of using a plasmid having a temperature sensitive replication origin, a method of using a plasmid capable of conjugative transfer, a method of utilizing a suicide vector not having a replication origin that functions in a host (U.S. Pat. No. 6,303,383, Japanese Patent Laid-open (Kokai) No. 05-007491), and so forth.

Modification for reducing activity of a protein can also be attained by, for example, a mutagenesis treatment. Examples of the mutagenesis treatment can include irradiation of X-ray or ultraviolet and treatment with a mutation agent such as N-methyl-N'-nitro-N-nitrosoguanidine (MNNG), ethyl methanesulfonate (EMS), and methyl methanesulfonate (MMS).

When a protein functions as a complex made up of a plurality of subunits, some or all of the subunits may be modified, so long as the activity of the protein is eventually reduced. That is, for example, some or all of the genes that encode the respective subunits may be disrupted or the like. Furthermore, when there is a plurality of isozymes of a protein, some or all of the activities of the plurality of isozymes may be reduced, so long as the activity of the protein is eventually reduced. That is, for example, some or all of the genes that encode the respective isozymes may be disrupted or the like.

A reduction in the activity of a protein can be confirmed by measuring the activity of the protein.

A reduction in the activity of a protein can also be confirmed by confirming a reduction in the expression of a gene encoding the protein. A reduction in the expression of a gene can be confirmed by confirming a reduction in the transcription amount of the gene or a reduction in the amount of the protein expressed from the gene.

A reduction in the transcription amount of a gene can be confirmed by comparing the amount of mRNA transcribed from the gene with that of a non-modified strain. Examples of the method for evaluating the amount of mRNA can include Northern hybridization, RT-PCR, and so forth (Molecular Cloning, Cold Spring Harbor Laboratory Press, Cold Spring Harbor (USA), 2001). The amount of mRNA may be reduced to, for example, 50% or less, 20% or less, 10% or less, 5% or less, or 0% of that of a non-modified strain.

A reduction in the amount of a protein can be confirmed by Western blotting using antibodies (Molecular Cloning, Cold Spring Harbor Laboratory Press, Cold Spring Harbor (USA) 2001). The amount of the protein may be reduced to, for example, 50% or less, 20% or less, 10% or less, 5% or less, or 0% of that of a non-modified strain.

Disruption of a gene can be confirmed by determining nucleotide sequence of a part or the whole of the gene, restriction enzyme map, full length, or the like of the gene depending on the means used for the disruption.

The aforementioned methods for reducing the activity of a protein as mentioned above can be applied to reduction in the activities of any proteins, such as enzymes that catalyze a reaction branching away from the biosynthesis pathway of an objective basic amino acid to generate a compound other than the objective basic amino acid, and reduction in the expression of any genes, such as genes encoding enzymes that catalyze a reaction branching away from the biosynthesis pathway of an objective basic amino acid to generate a compound other than the objective basic amino acid.

<2> Fermentation Step

The fermentation step is a step of culturing a microorganism having a basic amino acid-producing ability in a culture medium, to obtain a fermentation broth containing the basic amino acid. The fermentation step is carried out so that bicarbonate ions and/or carbonate ions serve as counter ions for the basic amino acid. Such a fermentation method can also be referred to as "carbonate fermentation". By the carbonate fermentation, a basic amino acid can be produced by fermentation while reducing the amount of sulfate ions and/or chloride ions that are used, which have been conventionally used as counter ions for a basic amino acid.

The carbonate fermentation can be carried out, for example, as described in US2002-0025564A, EP1813677A, and Japanese Patent Laid-open (Kokai) No. 2002-65287.

Specifically, the carbonate fermentation can be carried out, for example, so that there is a culture period where 20 mM or more, 30 mM or more, or 40 mM or more, of bicarbonate ions and/or carbonate ions are present in the culture medium. The above-exemplified concentrations each can be interpreted as the total concentration of bicarbonate ions and carbonate ions. The phrase "there is a culture period where bicarbonate ions and/or carbonate ions are present in a culture medium at a certain concentration" can mean that bicarbonate ions and/or carbonate ions are present in the culture medium at the certain concentration during at least a partial period of culture. That is, bicarbonate ions and/or carbonate ions may be present in the culture medium at the above-exemplified concentration over the entire period of culture or during a partial period of culture. The "partial period" is not particularly limited so long as a desired productivity of the basic amino acid is attained. The "partial period" may be, for example, a period of 10% or more, 20% or more, 30% or more, 50% or more, 70% or more, or 90% or more of the entire period of culture. When the culture is performed separately as seed culture and main culture, the term "entire period of culture" can refer to the entire period of the main culture. It is preferable that bicarbonate ions and/or carbonate ions are present in the culture medium at the above-exemplified concentration during a period where the basic amino acid is produced. That is, for example, when the fermentation step includes a stage of proliferating the basic amino acid-producing bacterium (growth period) and a stage of producing the basic amino acid (production period), bicarbonate ions and/or carbonate ions can be present in the culture medium at the above-exemplified concentration at least during the production period. The term "growth period" can refer to a period when the carbon source is utilized mainly for cell growth, and may specifically refer to a period until the time point of 3 hr, 6 hr, or 10 hr after the start of culture. The term "production period" can refer to a period when the carbon source is utilized mainly for production of a substance, and may specifically refer to a period from the time point of 3 hr, 6 hr, or 10 hr after the start of culture.

Bicarbonate ions and/or carbonate ions can be generated in the culture medium by controlling the internal pressure of the fermentation tank to be positive, supplying carbon dioxide gas into the culture medium, or a combination thereof. The internal pressure of the fermentation tank during fermentation can be controlled to be positive by, for example, making the gas supply pressure higher than the exhaust pressure. If the internal pressure of the fermentation tank is controlled to be positive, the carbon dioxide gas generated by fermentation dissolves in the culture medium to generate bicarbonate ions and/or carbonate ions, and these can serve as counter ions for the basic amino acid. The internal pressure of the fermentation tank may specifically be, for example, 0.03 to 0.2 MPa, 0.05 to 0.15 MPa, or 0.1 to 0.3 MPa, in terms of gauge pressure (pressure difference with respect to the atmospheric pressure). Carbon dioxide gas can be supplied to the culture medium by, for example, bubbling pure carbon dioxide gas or a mixed gas containing carbon dioxide gas into the culture medium. Examples of the mixed gas containing carbon dioxide gas can include a mixed gas containing 5% v/v or more of carbon dioxide gas. The internal pressure in the fermentation tank, supply volume of carbon dioxide gas, and limited aeration volume can be appropriately set according to various conditions such as pH of the culture medium, bicarbonate and/or carbonate ion concentration in the culture medium, and ammonia concentration in the culture medium.

In the conventional methods for producing a basic amino acid, a sufficient amount of ammonium sulfate and/or ammonium chloride is usually added to the culture medium as a source of counter ions for the basic amino acid, or sulfuric acid decomposition products and/or hydrochloric acid decomposition products of proteins etc. as nutrient components are added to the culture medium. Therefore, a large amount of sulfate ions and/or chloride ions is present in the culture medium, and the concentration of the weakly acidic carbonate ions is extremely low, i.e., it is at a ppm order.

By contrast, the carbonate fermentation has a feature that the amount of sulfate ions and/or chloride ions used is reduced so that carbon dioxide gas released by a microorganism during fermentation and/or carbon dioxide gas externally supplied is dissolved in the culture medium, and used as counter ions for the basic amino acid. That is, in the carbonate fermentation, one of the aspects is to reduce the amount of sulfate ions and/or chloride ions that are used, and therefore, it is not necessary to add sulfate ions or chloride ions to the culture medium in an amount larger than that required for growth of the basic amino acid-producing microorganism. Ammonium sulfate or the like can be fed to the culture medium at an early stage of the culture in an amount required for growth, and the feeding is terminated in the middle of the culture. Alternatively, ammonium sulfate or the like may be fed to the culture medium while maintaining the balance with respect to the amount of carbonate ions and/or bicarbonate ions dissolved in the culture medium. By reducing the amount of sulfate ions and/or chloride ions that are used, the concentration of sulfate ions and/or chloride ions in the culture medium can be lowered. By lowering the concentration of sulfate ions and/or chloride ions, bicarbonate ions and/or carbonate ions can be generated more easily in the culture medium. That is, in the carbonate fermentation, the pH of the culture medium for generating bicarbonate ions and/or carbonate ions in the culture medium in an amount required to serve as the counter ions for the basic amino acid can be suppressed to be lower compared with the conventional methods. The total molar concentration of sulfate ions and chloride ions contained in the culture medium may specifically be, for example, 900 mM or lower, 700 mM or lower, 500 mM or lower, 300 mM or lower, 200 mM or lower, or 100 mM or lower.

In the carbonate fermentation, the pH of the culture medium is not particularly limited so long as bicarbonate ions and/or carbonate ions are generated in the culture medium at a desired concentration, and a desired productivity of the basic amino acid is attained. The pH of the culture medium can be appropriately set according to various conditions such as pH of the culture medium, bicarbonate and/or carbonate ion concentration in the culture medium, and ammonia concentration in the culture medium. The pH of the culture medium may be controlled to, for example, 6.5 to 9.0, or 7.2 to 9.0, during the culture. The pH of the culture medium may be controlled to the above-exemplified value during at least a partial period of culture. That is, the pH of the culture medium may be controlled to the above-exemplified value over the entire period of culture or during a partial period of culture. The descriptions concerning the culture period where bicarbonate ions and/or carbonate ions are present in a culture medium can be applied mutatis mutandis to the "partial period" during which the pH of the culture medium is controlled. That is, for example, the pH of the culture medium may be controlled to the above-exemplified value during a period where the basic amino acid is produced. Furthermore, the pH of the culture medium may be, for example, 7.2 or higher, preferably 7.2 to 9.0, at the completion of culture. That is, the pH of the culture medium may be controlled so as to attain the above-exemplified value of pH at the completion of culture. The pH of the culture medium may be controlled, for example, directly by using the pH value per se as an indicator, or indirectly by controlling the total ammonia concentration (WO2006/038695).

Furthermore, the culture medium may contain anions other than bicarbonate ions and/or carbonate ions (also referred to as other anions). It is preferred that the concentrations of the other anions in the culture medium are low so long as they are present in amounts required for growth of the basic amino acid-producing microorganism. Examples of the other anions can include chloride ions, sulfate ions, phosphate ions, organic acid ions, and hydroxide ions. The total molar concentration of these other anions may specifically be, for example, 900 mM or lower, 700 mM or lower, 500 mM or lower, 300 mM or lower, 200 mM or lower, 100 mM or lower, 50 mM or lower, or 20 mM or lower.

Furthermore, the culture medium may contain cations other than the basic amino acid (also referred to as other cations). Examples of the other cations can include K ions, Na ions, Mg ions, and Ca ions originating in culture medium components. The total molar concentration of the other cations may specifically be, for example, 50% or lower, 10% or lower, 5% or lower, 2% or lower, of the molar concentration of the total cations.

In the carbonate fermentation, it is also preferable to control the total ammonia concentration in the culture medium to a concentration at which production of the basic amino acid is not inhibited (WO2006/038695, WO2015/050234). The term "total ammonia concentration" can refer to the total concentration of non-dissociated ammonia ($NH_3$) and ammonium ions ($NH_4^+$). Examples of the total ammonia concentration at which "production of the basic amino acid is not inhibited" can include, for example, a total ammonia concentration providing yield and/or productivity corresponding to 50% or more, 70% or more, or 90% or more, of the yield and/or productivity obtainable in the production of the basic amino acid under optimal conditions. The total ammonia concentration in the culture medium may specifically be, for example, 300 mM or lower, 250 mM or lower, 200 mM or lower, 100 mM or lower, or 50 mM or lower. The dissociation degree of ammonia decreases as the pH becomes higher. Non-dissociated ammonia is more toxic to microorganisms compared with ammonium ions. Therefore, the upper limit of the total ammonia concentration also depends on the pH of the fermentation broth. That is, as the pH of the fermentation broth increases, the acceptable total ammonia concentration decreases. Therefore, the total ammonia concentration at which "production of the basic amino acid is not inhibited" can be determined for each specific pH value. However, the total ammonia concentration range that is acceptable at the highest pH level during the culture can be used as the total ammonia concentration range over the entire period of culture. The total ammonia concentration in the culture medium may be controlled to the above-exemplified concentration during at least a partial period of culture. That is, the total ammonia concentration in the culture medium may be controlled to the above-exemplified concentration over the whole period of culture or during a partial period of culture. The descriptions concerning the culture period where bicarbonate ions and/or carbonate ions are present in a culture medium can be applied mutatis mutandis to the "partial period" during which the total ammonia concentration in the culture medium is controlled. That is, for example, the total ammonia concentration in the culture medium may be controlled to the above-exemplified concentration during a period where the basic amino acid is produced. Furthermore, specific examples of the "partial period" during which the total ammonia concentration in the culture medium can include a period during which the pH of the culture medium increases due to the shortage of counter ions such as sulfate ions and chloride ions with respect to accumulation of the basic amino acid.

Meanwhile, the total concentration of ammonia as a source of nitrogen required for growth of the basic amino acid-producing microorganism and production of the basic amino acid is not particularly limited, and can be appropriately set, so long as depletion of ammonia does not continue during the culture, and decrease in the productivity of the basic amino acid due to the shortage of the nitrogen source does not occur. For example, the ammonia concentration can be measured over time during the culture, and if ammonia in the culture medium is depleted, a small amount of ammonia can be added to the culture medium. The ammonia concentration after the addition of ammonia may specifically be, for example, 1 mM or higher, 10 mM or higher, or 20 mM or higher, as the total ammonia concentration.

The total ammonia concentration in the culture medium can be controlled by, for example, using an apparatus for controlling ammonia and a method for controlling ammonia described in WO2015/050234.

The culture medium is not particularly limited, so long as a basic amino acid is produced by the carbonate fermentation. The culture medium may contain various organic and inorganic components, such as a carbon source, nitrogen source, and trace nutrient, as required. The types and concentrations of the culture medium components can be appropriately determined according to various conditions such as the type of basic amino acid-producing microorganism and the type of basic amino acid to be produced.

The carbon source is not particularly limited, so long as the basic amino acid-producing microorganism can utilized it to produce a basic amino acid. Specific examples of the carbon source can include, for example, saccharides such as glucose, fructose, sucrose, lactose, galactose, arabinose, blackstrap molasses, hydrolysates of starches, and hydrolysates of biomass, organic acids such as acetic acid, fumaric acid, citric acid, succinic acid, and malic acid, alcohols such as ethanol, glycerol, and crude glycerol, hydrocarbons such as methane, and aliphatic acids. As the carbon source, a single kind of carbon source may be used, or two or more kinds of carbon sources may be used in combination.

Specific examples of the nitrogen source can include, for example, inorganic nitrogen sources such as ammonium salts, ammonia, and urea, and organic nitrogen sources such as peptone, yeast extract, meat extract, and soybean protein decomposition products. As the nitrogen source, a single kind of nitrogen source may be used, or two or more kinds of nitrogen sources may be used in combination.

Specific examples of the trace nutrient can include, for example, amino acids, vitamins, and trace metal elements. As the trace nutrient, a single kind of ingredient may be used, or two or more kinds of ingredients may be used in combination.

When an auxotrophic mutant that requires an amino acid or the like for growth thereof is used, a required nutrient can be supplied to the culture medium. For example, in many of L-lysine-producing microorganisms, the L-lysine biosynthetic pathway is enhanced and the L-lysine decomposition ability is attenuated. When such an L-lysine-producing microorganism is cultured, for example, one or more of L-threonine, L-homoserine, L-isoleucine, and L-methionine can be added to the culture medium.

The culture conditions are not particularly limited, so long as a basic amino acid is produced by the carbonate fermentation. The culture conditions may be appropriately determined according to various conditions such as the type of basic amino acid-producing microorganism. The culture can be performed, for example, aerobically by aeration culture or shaking culture using a liquid medium. The culture temperature may be, for example, 20 to 45° C., or 25 to 37° C. The culture period may be, for example, 10 to 120 hours. The culture can be performed as batch culture, fed-batch culture, continuous culture, or a combination of these. Furthermore, cells of the microorganism can be collected from the fermentation broth and reused (French Patent No. 2669935). The culture may also be performed separately as pre-culture and main culture.

By culturing the basic amino acid-producing microorganism as described above, a basic amino acid accumulates in the culture medium, and thereby a fermentation broth containing the basic amino acid is obtained. The fermentation broth further can contain bicarbonate ions and/or carbonate ions. Bicarbonate ions and/or carbonate ions present in the fermentation broth may function as counter ions of the basic amino acid. That is, the expression "the fermentation step is carried out so that bicarbonate ions and/or carbonate ions serve as counter ions for the basic amino acid" may specifically mean that a fermentation broth containing bicarbonate ions and/or carbonate ions is obtained by the fermentation step. The concentration of bicarbonate ions and/or carbonate ions present in the fermentation broth is not particularly limited. The concentration of bicarbonate ions and/or carbonate ions present in the fermentation broth may be, for example, 20 mM or more, 30 mM or more, or 40 mM or more. The above-exemplified concentrations each are interpreted as the total concentration of bicarbonate ions and carbonate ions. The concentration of bicarbonate ions and/or carbonate ions present in the fermentation broth may also be, for example, such a concentration that the normality ratio shown in the following equation is 5 or more, 10 or more, or 20 or more, and 100 or less, 90 or less, or 80 or less, or to be within a range defined by any combination of these ranges.

Normality ratio=(Normality of bicarbonate ions and carbonate ions/Normality of total cations)×100

Production of the basic amino acid can be confirmed by known methods used for detection or identification of compounds. Examples of such methods can include, for example, HPLC, LC/MS, GC/MS, and NMR. These methods can be independently used, or can be used in an appropriate combination.

<3> Pressurized Heat Treatment Step

The pressurized heat treatment step is a step of subjecting the fermentation broth obtained in the fermentation step to a heat treatment under a pressure sufficient for preventing generation of carbon dioxide gas from the fermentation broth. This treatment can also be referred to as "pressurized heat treatment". The pressurized heat treatment step is, in other words, a step of heating the fermentation broth obtained in the fermentation step while applying thereon a pressure sufficient for preventing generation of carbon dioxide gas from the fermentation broth. In the pressurized heat treatment step, generation of carbon dioxide gas from the fermentation broth due to heating can be prevented by pressurization. The phrase "generation of carbon dioxide gas from a fermentation broth" can mean that carbon dioxide substances dissolved in the fermentation broth gasify and are released from the fermentation broth. The term "carbon dioxide substances" collectively can refer to carbon dioxide molecule, carbonic acid molecule, carbonate ion, and bicarbonate ion. Generation of carbon dioxide gas from the fermentation broth can also be referred to as "decarboxylation".

The minimum pressure required for preventing generation of carbon dioxide gas from the fermentation broth can also be referred to as "required pressure". That is, the pressure of the pressurized heat treatment can be equal to or higher than the required pressure. The pressure of the pressurized heat treatment is not particularly limited, so long as it is equal to or higher than the required pressure. The pressure of the pressurized heat treatment may be, for example, 101% or more, 103% or more, 105% or more, 110% or more, 115% or more, 120% or more, or 130% or more of the required pressure, for sufficiently preventing generation of carbon dioxide gas from the fermentation broth. The term "pressure" can refer to gauge pressure, that is the pressure difference with respect to the atmospheric pressure, unless otherwise stated.

The required pressure can be appropriately determined according to various conditions such as the composition of the fermentation broth, the pH of the fermentation broth, and the temperature of the pressurized heat treatment.

The required pressure can be calculated (determined), specifically, for example, using the concentration(s) of component(s) in the fermentation broth, such as the basic amino acid, $CO_2$, $NH_3$, K, Mg, Cl, $SO_4$, acetic acid, and succinic acid, and the temperature as variables. That is, first, the pH of the fermentation broth at a certain temperature can be calculated using the concentration(s) of component(s) in the fermentation broth, such as the basic amino acid, $CO_2$, $NH_3$, K, Mg, Cl, $SO_4$, acetic acid, and succinic acid, and the temperature as variables. Next, the dissociative state of the basic amino acid can be determined using the pH and the temperature as variables. Assuming that $HCO_3$ ions unable to retain the basic amino acid as counter ions at the temperature of the pressurized heat treatment (i.e. $HCO_3$ ions that lost counter ions due to heating) gasify, the abundance ratio (existing rate) of $HCO_3$ ions unable to retain the basic amino acid as counter ions at the temperature of the pressurized heat treatment can be calculated on the basis of the dissociative state of the basic amino acid, the concentration of the basic amino acid, and the concentration of $CO_2$, and the partial pressure of carbon dioxide can be calculated according to Henry's law. That is, the partial pressure of carbon dioxide can be calculated using the concentration(s) of component(s) in the fermentation broth, such as the basic amino acid, $CO_2$, $NH_3$, K, Mg, Cl, $SO_4$, acetic acid, and succinic acid, and the temperature as variables. The type(s) of component(s) used as variable(s) is/are not particularly limited, so long as the required pressure can be determined. The type(s) of component(s) used as variable(s) can be appropriately determined according to various conditions such as the composition of the fermentation broth. For example, some of or all of the components such as the basic amino acid, $CO_2$, $NH_3$, K, Mg, Cl, $SO_4$, acetic acid, and succinic acid, can be used as variable(s). Specific examples of some of the components can include, for example, the basic amino acid, $CO_2$, $NH_3$, Cl, and $SO_4$. The partial pressure of water vapor can be calculated by, for example, using the Wagner equation. The total value of the partial pressure of carbon dioxide and the partial pressure of water vapor can be regarded as the required pressure. Specifically, for example, when the basic amino acid is L-lysine, the required pressure can be calculated according to the procedures described in Example 2. Also when using basic amino acids other than L-lysine, the required pressure can be calculated according to the procedures described in Example 2 with appropriate modification. The concentration of each component can be determined by, for example, such known methods used for detection or identification of compounds as described above. In addition, particularly, the concentration of each ion can be determined by, for example, ion chromatography.

In addition, by using the aforementioned procedures, the required pressure for a specific composition of fermentation broth can also be obtained as an approximate equation. Specifically, for example, the required pressure for the lysine fermentation broth shown in Table 5 described later can be expressed as the following equation (Example 4). In the equation, "temperature" represents the temperature (° C.) of the pressurized heat treatment.

Required pressure (kPa)=$1.99 \times 10^{-3} \times$ temperature$^{2.54}$

Alternatively, the required pressure can be measured. That is, the pressure of the pressurized heat treatment may be equal to or higher than, for example, the required pressure to be measured. The required pressure can be measured, specifically, as the pressure of a gas phase in a sealed vessel observed when the fermentation broth is put in the sealed vessel and adjusted (heated) to the temperature of the pressurized heat treatment. That is, the term "required pressure to be measured" may specifically refer to the pressure of a gas phase in a sealed vessel observed when the fermentation broth is put in the sealed vessel and adjusted (heated) to the temperature of the pressurized heat treatment. Examples of such a sealed vessel can include TEM-V Series reactors (Taiatsu Techno). The volume of the fermentation broth put in the sealed vessel is not particularly limited, so long as the required pressure can be measured with desired accuracy. The fermentation broth may be put in the sealed vessel, for example, so that the porosity of apparatus comes to be such a value as described below. The term "porosity of apparatus" can refer to the ratio of the volume of the gas phase in the sealed vessel with respect to the internal volume of the sealed vessel. The porosity of apparatus can be low. The porosity of apparatus may be, for example, 2% v/v to 10% v/v, or specifically 6% v/v. The initial gas phase (the gas phase before heating) in the aforementioned measurement method shall be air.

The required pressure may be determined every time (every time when the fermentation step is carried out), or may be preliminarily determined. When the required pressure is preliminarily determined, the required pressure can be determined using, for example, a fermentation broth obtained in a similar manner or a model fermentation broth prepared as a similar composition. The method as described herein may or may not include a step of determining the required pressure (also referred to as "pressure-determining step"). The pressure-determining step can be carried out before the step (B). Incidentally, regarding the meaning of the expression "the pressure of the pressurized heat treatment is equal to or higher than the required pressure to be determined by a certain means", it is sufficient that the pressure of the pressurized heat treatment is equal to or higher than the required pressure that should be obtained provided that the certain means is used, regardless whether or not the certain means is actually used.

The pressure of the pressurized heat treatment may specifically be, for example, 100 kPa or higher, 200 kPa or higher, 300 kPa or higher, 400 kPa or higher, 500 kPa or higher, 600 kPa or higher, 700 kPa or higher, 800 kPa or higher, 900 kPa or higher, 1000 kPa or higher, 1100 kPa or higher, or 1200 kPa or higher. The upper limit of the pressure of the pressurized heat treatment is not particularly limited, and it is sufficient that the pressure is equal to or lower than the maximum pressure usable in the apparatus to be used. The pressure of the pressurized heat treatment may specifically be, for example, 3000 kPa or lower, 2000 kPa or lower, or 1500 kPa or lower. The pressure of the pressurized heat treatment may also be within a range defined by any combination of aforementioned ranges.

Whether the pressurized heat treatment was carried out with a pressure sufficient for preventing generation of carbon dioxide gas from the fermentation broth, i.e. whether the pressure of the pressurized heat treatment was a pressure sufficient for preventing generation of carbon dioxide gas from the fermentation broth, can be judged on the basis of, for example, change in the pH of the fermentation broth before and after the pressurized heat treatment. That is, the pH of the fermentation broth rises if carbon dioxide gas is generated from the fermentation broth. Hence, for example, when the increased value of the pH of the fermentation broth observed upon carrying out the pressurized heat treatment under a certain pressure is 0.3 or less, 0.2 or less, 0.1 or less, or 0.05 or less, the certain pressure can be judged as a pressure sufficient for preventing generation of carbon dioxide gas from the fermentation broth. Also, whether the pressurized heat treatment was carried out with a pressure sufficient for preventing generation of carbon dioxide gas from the fermentation broth, i.e. whether the pressure of the pressurized heat treatment was a pressure sufficient for preventing generation of carbon dioxide gas from the fermentation broth, can be confirmed by, for example, confirming the presence or absence of foaming of carbon dioxide gas from the fermentation broth upon the pressurized heat treatment. That is, when foaming of carbon dioxide gas from the fermentation broth is not observed upon carrying out the pressurized heat treatment under a certain pressure, the certain pressure can be judged as a pressure sufficient for preventing generation of carbon dioxide gas from the fermentation broth.

The temperature of the pressurized heat treatment is not particularly limited, so long as an effect of preventing a decrease in the contained amount of the basic amino acid is obtained. The temperature of the pressurized heat treatment is higher than the temperature of the fermentation broth obtained by the fermentation step, i.e. higher than the culture temperature. The temperature of the pressurized heat treatment may be a temperature at which the basic amino acid-producing microorganism in the fermentation broth is sterilized. That is, the pressurized heat treatment may also serve as a sterilization treatment. The temperature of the pressurized heat treatment, for example, may be 60° C. or higher, 80° C. or higher, 100° C. or higher, 105° C. or higher, 110° C. or higher, 115° C. or higher, 120° C. or higher, or 125° C. or higher, may be 150° C. or lower, 140° C. or lower, 135° C. or lower, or 130° C. or lower, or may be within a range defined by any combination of these ranges. The temperature of the pressurized heat treatment may also be, for example, 60° C. to 130° C., 80° C. to 130° C., 100° C. to 130° C., 110° C. to 130° C., or 115° C. to 125° C.

Means for carrying out the pressurized heat treatment are not particularly limited. The pressurized heat treatment can be carried out in an appropriate vessel with which heating and pressurizing can be attained. Such a vessel can also be referred to as "pressure vessel". The pressurized heat treatment is carried out under conditions where substantially no gas phase is present in the pressure vessel. That is, in other words, the pressurized heat treatment is carried out under conditions where the pressure vessel is substantially filled with the fermentation broth. The expression "substantially no gas phase is present in a pressure vessel" means that the volume of a gas phase present in the pressure vessel upon the pressurized heat treatment is 1% v/v or lower, 0.5% v/v or lower, 0.1% v/v or lower, or 0 of the internal volume of the sealed vessel. The pressurized heat treatment can be carried out by, for example, supplying the fermentation broth under pressurization into the pressure vessel, or pressurizing the fermentation broth filled in the pressure vessel using a piston or the like. At this time, the fermentation broth in the pressure vessel is heated. For example, the fermentation broth may be heated using a heating function equipped in the pressure vessel, or the fermentation broth may be heated together with the pressure vessel from the outside of the pressure vessel using external heating equipment. The form and type of the pressure vessel are not particularly limited. Examples of the pressure vessel can include a retention pipe or tube (a pipe or tube for retaining an object therein) and a tank. That is, for example, it is sufficient that the fermentation broth is supplied into the pressure vessel, such as a retention pipe or tube, with a liquid feed pressure equal to or higher than the required pressure. Introduction of the fermentation broth into the pressure vessel and discharge of the fermentation broth from the pressure vessel can be carried out intermittently or continuously so that a certain retention time (treatment period) is obtained. That is, the pressurized heat treatment may be carried out by, for example, a continuous method or a batch method. By carrying out the pressurized heat treatment with a pressure equal to or higher than the required pressure, generation of carbon dioxide gas from the fermentation broth can be prevented. When the pressurized heat treatment is carried out by a continuous method, by preventing generation of carbon dioxide gas from the fermentation broth, an auxiliary effect that the flow rate can be kept constant is also obtained.

The period of the pressurized heat treatment is not particularly limited, so long as an effect of preventing a decrease in the contained amount of the basic amino acid is obtained. The period can be appropriately determined according to various conditions such as the temperature and pressure of the pressurized heat treatment. The period of the pressurized heat treatment may be a period with which the basic amino acid-producing microorganism in the fermentation broth is sterilized. The period of the pressurized heat treatment, for example, may be 30 seconds or longer, 1 minute or longer, 2 minutes or longer, 3 minutes or longer, 5 minutes or longer, or 10 minutes or longer, and may be 120 minutes or shorter, 90 minutes or shorter, 60 minutes or shorter, 30 minutes or shorter, or 15 minutes or shorter, or may be within a range defined by any combination of these ranges. The period of the pressurized heat treatment may also be, for example, 30 seconds to 60 minutes, 1 minute to 30 minutes, or 2 minutes to 15 minutes. When the pressurized heat treatment is carried out by a continuous method, it is sufficient that the flow rate is determined so that a certain treatment period is obtained.

By the pressurized heat treatment, a decrease in the amount of the basic amino acid present can be prevented. The term "amount of a basic amino acid" can refer to the amount, such as the concentration, of the basic amino acid present in the fermentation broth. Examples of the "prevention of a decrease in the amount of a basic amino acid present" can include prevention of a decrease in the amount of the basic amino acid present during the pressurized heat treatment and after the pressurized heat treatment. Specific examples of the "prevention of a decrease in the amount of a basic amino acid present" can include prevention of a decrease in the amount of the basic amino acid present upon heating during the pressurized heat treatment and heating after the pressurized heat treatment. Specific examples of the "prevention of a decrease in the amount of a basic amino acid present after the pressurized heat treatment" can include prevention of a decrease in the amount of the basic amino acid present upon carrying out a treatment such as decarboxylation after the pressurized heat treatment. Prevention of a decrease in the amount of the basic amino acid present after the pressurized heat treatment may be due to sterilization of the basic amino acid-producing microorganism in the fermentation broth during the pressurized heat treatment.

By the pressurized heat treatment, a fermentation broth treated with the pressurized-heat-treatment (pressurized-heat-treated fermentation broth) is obtained.

<4> Other Treatments

The pressurized-heat-treated fermentation broth may further be subject to another treatment. Examples of the other treatment can include decarboxylation, cell removal, purification, concentration, and drying. These treatments may be carried out independently or in any appropriate combination. The expression "a pressurized-heat-treated fermentation broth is further subject to another treatment" is not limited to cases where the pressurized-heat-treated fermentation broth per se is subject to another treatment, but also can include cases where a further treated product of the pressurized-heat-treated fermentation broth is subject to another treatment. That is, for example, the expression "a pressurized-heat-treated fermentation broth is further subject to a decarboxylation treatment" is not limited to cases where the pressurized-heat-treated fermentation broth per se is subject to a decarboxylation treatment, but also can include cases where the pressurized-heat-treated fermentation broth is subject to a treatment other than decarboxylation treatment, such as cell removal, and then subject to a decarboxylation treatment. In the present invention, the term "fermentation product" includes the pressurized-heat-treated fermentation broth per se, and any products obtained from the same and containing the basic amino acid. Specific examples of the "fermentation product" can include the fermentation broth (herein, the pressurized-heat-treated fermentation broth), a supernatant of the fermentation broth, decarboxylation products thereof, concentrated products thereof, dried products thereof, and processed products thereof. Specific examples of such dried or processed products can include dried granulated products containing the basic amino acid.

The decarboxylation treatment can be carried out by, for example, heating, concentration, depressurization, pH reduction, or a combination thereof. The means for the decarboxylation treatment can be appropriately selected according to, for example, various conditions such as the type of the product to be produced. As the means for the decarboxylation treatment, particularly, heating is a example. When the decarboxylation treatment is carried out by a means other than depressurization, the decarboxylation treatment may be carried out, for example, under atmospheric pressure (i.e. in an open system). When the decarboxylation treatment is carried out by heating, the temperature of heating is not particularly limited, and it may be, for example, 40° C. to 100° C., or 60° C. to 90° C. When the decarboxylation treatment is carried out by depressurization, the pressure in the gas phase during depressurization is not particularly limited, and it may be, for example, 600 kPa or lower, or 40 kPa to 200 kPa, in terms of absolute pressure. A pH reduction can be carried out by addition of a strong acid, such as hydrochloric acid. By the decarboxylation treatment, carbon dioxide substances, such as bicarbonate ions and carbonate ions, can be removed from the fermentation broth. That is, the term "decarboxylation product" can refer to a product from which carbon dioxide substances, such as bicarbonate ions and carbonate ions, have been removed. When the decarboxylation treatment is carried out by a means other than pH reduction, the pH rises due to decarboxylation. However, it is expected that a decrease in the amount of the basic amino acid present in the fermentation broth is sufficiently prevented after the pressurized heat treatment even if the pH rises.

The cell removal treatment can be carried out by, for example, centrifugation, filtration, or a combination thereof.

Collection (purification) of the basic amino acid can be carried out by known methods used for separation and purification of compounds. Examples of such methods can include, for example, ion-exchange resin method, membrane treatment method, precipitation method, and crystallization method. These methods can be used independently or in any appropriate combination. When the basic amino acid is accumulated also in cells of the microorganism, for example, the cells can be disrupted with ultrasonic waves or the like, a supernatant can be obtained by removing the cells from the cell-disrupted suspension by centrifugation, and the basic amino acid can be collected from the supernatant by the ion exchange resin method or the like. When the basic amino acid is precipitated in the culture medium, it can be collected by centrifugation, filtration, or the like. The basic amino acid precipitated in the culture medium may also be collected together with the basic amino acid dissolving in the culture medium, after the basic amino acid dissolving in the culture medium is crystallized. The basic amino acid to be collected may be a free compound, a salt thereof, or a mixture thereof. That is, the term "basic amino acid" may refer to the amino acid as a free compound, a salt thereof, or a mixture thereof. Examples of the salt can include, for example, carbonate, bicarbonate, hydrochloride, and sulfate.

The collected basic amino acid may be present in a mixture that also contains, for example, such components as microbial cells, culture medium components, moisture, and by-product metabolites of the microorganism, in addition to the basic amino acid. The basic amino acid may also be purified to a desired extent. The purity of the collected basic amino acid may be, for example, 30% (w/w) or higher, 50% (w/w) or higher, 70% (w/w) or higher, 80% (w/w) or higher, 90% (w/w) or higher, or 95% (w/w) or higher.

The basic amino acid may be provided as, for example, a dried granulated product containing the basic amino acid. For example, L-lysine may be provided as, for example, a dried granulated product containing L-lysine.

Examples of methods for producing a dried granulated product containing L-lysine can include the method described in U.S. Pat. No. 7,416,740. Specifically, a dried granulated product containing L-lysine can be produced by using an L-lysine fermentation broth having an equivalent ratio of anion/L-lysine of 0.68 to 0.95, 0.68 to 0.90, or 0.68 to 0.86 as a raw material. The term "equivalent ratio of anion/L-lysine" can refer to a value calculated on the basis of the following equation from the amounts of L-lysine (L-Lys), sulfate ion, chloride ion, ammonium ion, sodium ion, potassium ion, magnesium ion, and calcium ion. In the equation, "[ ]" represents the molar concentration.

$$\text{Equivalent ratio of anion/L-lysine} = (2\times[SO_4^{2-}] + [Cl^-] - [NH_4^+] - [Na^+] - [K^+] - 2\times[Mg^{2+}] - 2\times[Ca^{2+}])/[L\text{-}Lys]$$

That is, the equivalent ratio of anion/L-lysine of the pressurized-heat-treated L-lysine fermentation broth can be adjusted to be within the range exemplified above as required, and then a dried granulated product containing L-lysine can be produced. The equivalent ratio of anion/L-lysine can be increased by, for example, addition of hydrochloric acid or sulfuric acid, addition of an L-lysine aqueous solution having a high equivalent ratio of anion/L-lysine (e.g. higher than 0.95), or both. Examples of the L-lysine aqueous solution having an equivalent ratio of anion/L-lysine higher than 0.95 can include L-lysine aqueous solutions of which the pH is neutral to acidic, such as L-lysine aqueous solutions obtainable by a fermentation method other than the carbonate fermentation. The equivalent ratio of anion/L-lysine can be decreased by, for example, addition of an L-lysine aqueous solution having a low equivalent ratio of anion/L-lysine (e.g. lower than 0.68). Examples of the L-lysine aqueous solution having an equivalent ratio of anion/L-lysine lower than 0.68 can include an aqueous solution of L-lysine base (L-lysine as a free compound). Also, the pressurized-heat-treated L-lysine fermentation broth may be subject to a treatment such as decarboxylation and concentration, and then used for production of a dried granulated product. By this method, a dried granulated product containing L-lysine and having an equivalent ratio of anion/L-lysine of 0.68 to 0.95, 0.68 to 0.90, or 0.68 to 0.86 is obtained. The amount of L-lysine present in this dried granulated product may be, for example, 40 to 85%, 50 to 85%, or 60 to 85% by weight with respect to the total solid in this dried granulated product. The moisture content of this dried granulated product may be, for example, 5% or lower by weight with respect to the total amount of this dried granulated product. Production of a dried granulated product from the pressurized-heat-treated L-lysine fermentation broth can be carried out by known methods used for production of a dried granulated product containing an L-amino acid. Examples of such methods can include, for example, a method of solidifying a fermentation broth and then subjecting the solidified product to granulation, and a method of directly granulating and drying a fermentation broth using a seed (U.S. Pat. No. 7,416,740).

EXAMPLES

Hereinafter, the present invention will be more specifically explained with reference to examples.

Reference Example 1

Temperature Dependency of Decrease in Lysine Concentration in Lysine Fermentation Broth The carbonate fermentation was carried out in accordance with the method described in US2002-025564A, to obtain a fermentation broth of pH8.3 containing lysine (also referred to as "lysine fermentation broth"). The lysine fermentation broth was put in a reactor and stirred at 20° C., 40° C., or 60° C., and transition of the lysine concentration was confirmed. The results are shown in Table 1. In the Table, the lysine concentration is shown as a relative value with respect to the initial lysine concentration (=lysine concentration/initial lysine concentration). A higher temperature resulted in faster progress of a decrease in the lysine concentration, and the decreasing rate was lowered with the elapse of time. The lysine concentration was measured with HPLC (the same shall apply hereinafter).

TABLE 1

Transition of lysine concentration

| | | | Lysine concentration (lysine concentration/initial lysine concentration) | | | | | |
|---|---|---|---|---|---|---|---|---|
| No | Temperature | pH | 0 hr | 1 hr | 2 hr | 4 hr | 8 hr | 24 hr |
| 1 | 20° C. | 8.3 | 1.0 | 1.0 | 1.0 | 1.0 | 1.0 | $9.9 \times 10^{-1}$ |
| 2 | 40° C. | 8.3 | 1.0 | 1.0 | $9.9 \times 10^{-1}$ | $9.8 \times 10^{-1}$ | $9.8 \times 10^{-1}$ | $9.7 \times 10^{-1}$ |
| 3 | 60° C. | 8.3 | 1.0 | $9.8 \times 10^{-1}$ | $9.8 \times 10^{-1}$ | $9.7 \times 10^{-1}$ | $9.6 \times 10^{-1}$ | $9.4 \times 10^{-1}$ |

Reference Example 2 pH Dependency of Decrease in Lysine Concentration in Lysine Fermentation Broth

HCl was added to the lysine fermentation broth (pH8.3) obtained in Reference Example 1, to prepare lysine fermentation broths of pH4.5, pH5.5, and pH7.0. The lysine fermentation broth (pH8.3) and the pH-adjusted lysine fermentation broths (pH4.5, pH5.5, and pH7.0) each were stirred at 60° C., and transition of the lysine concentration was confirmed. The results are shown in Table 2. In the Table, the lysine concentration is shown as a relative value with respect to the initial lysine concentration (=lysine concentration/initial lysine concentration). A higher pH resulted in faster progress of a decrease in the lysine concentration, and no decrease in the lysine concentration progressed at pH5.5 or lower.

TABLE 2

Transition of lysine concentration

| | | | Lysine concentration (lysine concentration/initial lysine concentration) | | | | | |
|---|---|---|---|---|---|---|---|---|
| No | Temperature | pH | 0 hr | 1 hr | 2 hr | 4 hr | 16 hr | 24 hr |
| 1 | 60° C. | 8.3 | 1.0 | $9.7 \times 10^{-1}$ | $9.7 \times 10^{-1}$ | $9.7 \times 10^{-1}$ | $9.6 \times 10^{-1}$ | $9.5 \times 10^{-1}$ |
| 2 | 60° C. | 7.0 | 1.0 | 1.0 | $9.9 \times 10^{-1}$ | $9.9 \times 10^{-1}$ | $9.8 \times 10^{-1}$ | $9.7 \times 10^{-1}$ |
| 3 | 60° C. | 5.5 | 1.0 | $9.9 \times 10^{-1}$ | 1.0 | 1.0 | 1.0 | 1.0 |
| 4 | 60° C. | 4.5 | 1.0 | 1.0 | 1.0 | 1.0 | 1.0 | 1.0 |

Example 1

Suppression of Decrease in Lysine Concentration Under High Pressure

The lysine fermentation broth (pH8.3) obtained in Reference Example 1 was subject to a pressurized heat treatment in a retention pipe (retention tube) under the following conditions: at a temperature of 60° C. under a pressure of 0.1 MPa, at a temperature of 120° C. under a pressure of 0.2 MPa, or at a temperature of 120° C. under a pressure of 1.5 MPa, and transition of the lysine concentration before and after the treatment and the pH before and after the treatment were confirmed. The results are shown in Table 3. In the Table, the lysine concentration is shown as a relative value with respect to the initial lysine concentration (=lysine concentration/initial lysine concentration). Under the conditions with a temperature of 60° C. and a pressure of 0.1 MPa (experimental conditions 1 and 2) and the conditions with a temperature of 120° C. and a pressure of 0.2 MPa (experimental conditions 3, 4, 5, 6, and 7), a decrease in the lysine concentration progressed. By contrast, under the conditions with a temperature of 120° C. and a pressure of 1.5 MPa (experimental conditions 8 and 9), a decrease in the lysine concentration was suppressed. It was shown that carbon dioxide gas was generated from the lysine fermentation broth under the conditions with a temperature of 60° C. and a pressure of 0.1 MPa (experimental conditions 1 and 2) and the conditions with a temperature of 120° C. and a pressure of 0.2 MPa (experimental conditions 3, 4, 5, 6, and 7), since an increase in the pH was observed. By contrast, it was shown that generation of carbon dioxide gas from the lysine fermentation broth was prevented under the conditions with a temperature of 120° C. and a pressure of 1.5 MPa (experimental conditions 8 and 9), since no increase in the pH was observed. From the above, it was revealed that by subjecting a fermentation broth obtainable by the carbonate fermentation and containing a basic amino acid to a heat treatment under a pressure sufficient for preventing generation of carbon dioxide gas from the fermentation broth, a decrease in the amount of the basic amino acid present in the fermentation broth during the heat treatment can be prevented.

TABLE 3

| | | | | Lys concn. | | pH | | Lysine decomposition |
|---|---|---|---|---|---|---|---|---|
| Cond. | Temp. ° C. | Press. Mpa | Time Min | Before treatment | After treatment | Before treatment | After treatment | ratio % |
| 1 | 60° C. | 0.1 | 60 | 1.0 | $9.8 \times 10^{-1}$ | 8.3 | — | 1.9% |
| 2 | 60° C. | 0.1 | 60 | 1.0 | $9.7 \times 10^{-1}$ | 8.3 | — | 2.7% |
| 3 | 120° C. | 0.2 | 20 | 1.0 | $9.8 \times 10^{-1}$ | 8.2 | 9.1 | 1.7% |
| 4 | 120° C. | 0.2 | 20 | 1.0 | $9.8 \times 10^{-1}$ | 8.2 | 8.8 | 1.7% |

TABLE 3-continued

|  | Temp. °C. | Press. Mpa | Time Min | Lys concn. | | pH | | Lysine decomposition ratio % |
|---|---|---|---|---|---|---|---|---|
| Cond. | | | | Before treatment | After treatment | Before treatment | After treatment | |
| 5 | 120° C. | 0.2 | 20 | 1.0 | $9.8 \times 10^{-1}$ | 8.1 | 8.7 | 2.0% |
| 6 | 120° C. | 0.2 | 20 | 1.0 | $9.7 \times 10^{-1}$ | 8.5 | 10 | 3.5% |
| 7 | 120° C. | 0.2 | 20 | 1.0 | $9.7 \times 10^{-1}$ | 8.2 | 10 | 3.2% |
| 8 | 120° C. | 1.5 | 3 | 1.0 | 1.0 | 8.1 | 7.8 | −0.3% |
| 9 | 120° C. | 1.5 | 3 | 1.0 | 1.0 | 8.3 | 8.1 | −0.1% |

Temp., Temperature
Press., Pressure
Lys concn., Lysine concentration (concentration/initial concentration)
Cond., Experimental conditions Example 2

Calculation of Pressure Required for Preventing Generation of Carbon Dioxide Gas from Lysine Fermentation Broth The pressure required for preventing generation of carbon dioxide gas from the lysine fermentation broth was calculated using an equation according to the following procedures.

<1> pH Simulation

The pressure required for preventing generation of carbon dioxide gas from the fermentation broth depends on the dissociative state of each ion contained in the fermentation broth. The dissociative state of each ion contained in the fermentation broth depends on the pH of the fermentation broth. Hence, for calculating the pressure required for preventing generation of carbon dioxide gas from the fermentation broth, it is necessary to determine the pH of the fermentation broth for determining the dissociative state of each ion contained in the fermentation broth. The pH of the fermentation broth can depend on the temperature of the fermentation broth. However, pH measurement under conditions with a temperature of over 100° C. requires pressure-resistant sealed apparatus, direct measurement of the pH of the fermentation broth under such high-temperature conditions is difficult. Therefore, first, an equation for calculating the pH of the fermentation broth at each temperature was derived.

<1-1> Relationship Between Acid Dissociation Constant K and Temperature

The relationship shown in the following equation (1) holds for the Gibbs free energy and the equilibrium constant (acid dissociation constant K).

$$\Delta G = -RT \times \ln K \quad (1)$$

The relationship shown in the following equation (2) holds for the Gibbs free energy and enthalpy change.

$$\left(\frac{\partial (\Delta G/T)}{\partial T}\right)_P = \frac{\Delta H}{T^2} \quad (2)$$

The following equation (3) was obtained from the equations (1) and (2). The equation (3) indicates that the acid dissociation constant K is a function of the temperature.

$$\left(\frac{\partial \ln K}{\partial T}\right)_P = -\frac{\Delta H}{RT^2} \quad (3)$$

Hence, for Lys and $CO_2$ among ions contained in the lysine fermentation broth, wherein Lys and $CO_2$ are assumed to significantly affect the calculation of the required pressure when the dissociation equilibrium changes in a neutral to weak alkaline pH region depending on the temperature, the pK values shown in the following equations (4-1) to (4-5) (L. N. Plummer and E. Busenberg. Geochim. Cosmochim. Acta 46, 1011-1040 (1982)) were used as the pK values including a temperature factor. By deformation of the equations (4-1) to (4-5), the acid dissociation constant K is obtained as a function of the temperature.

$$pK_{Lys,1} = \exp\left(\frac{-0.0363 \times 1000}{Temp.\ [K]} + 0.8355\right) \quad (4-1)$$

$$pK_{Lys,2} = \exp\left(\frac{-0.2382 \times 1000}{Temp.\ [K]} + 1.402\right) \quad (4-2)$$

$$pK_{Lys,3} = \exp\left(\frac{-0.2372 \times 1000}{Temp.\ [K]} + 1.5686\right) \quad (4-3)$$

$$\ln K_{CO_2,1} = -820.438 + \frac{50275.82}{Temp.\ [K]} + 126.8339 \times \ln Temp.\ [K] - 0.142736 \times Temp.\ [K] - \frac{3879685}{(Temp.\ [K])^2} \quad (4-4)$$

$$\ln K_{CO_2,2} = -248.4208 + \frac{11862.51}{Temp.\ [K]} + 38.92561 \times \ln Temp.\ [K] - 0.0749001 \times Temp.\ [K] - \frac{1298007}{(Temp.\ [K])^2} \quad (4-5)$$

<1-2> pH Simulation

The pH was simulated using the acid dissociation constants K of Lys and $CO_2$ obtained above. For the simulation, the concentrations of $NH_3$, K, Mg, Cl, $SO_4$, acetic acid, and succinic acid, which can be contained in the lysine fermentation broth at large amounts, were also used, as well as Lys and $CO_2$. While it was assumed that the acid dissociation constants K of $NH_3$ and organic acids each are also a function of the temperature, in the simulation, $NH_3$ was treated as if $pK_{NH3}$ is 9.24 (constant value), and organic acids each were treated as a monovalent strong acid.

Since the total ion concentration in a solution fulfills the electrical neutrality, the following equation (5) is obtained. In the equation, each "C" represents the molar concentration (the same shall apply hereinafter).

$$f(C_{H^+}) = (2 \times C_{Lys^{++}} + C_{Lys^+} + C_{NH4^+} + C_{H^+} + C_{K^+} + 2 \times C_{Mg^{++}}) - (C_{Lys^-} + C_{OH^-} + 2 \times C_{CO3^{--}} + C_{HCO3^-} + C_{Cl^-} + 2 \times C_{SO4^{--}} + 2 \times C_{Suc.^{--}} + C_{Ace.^-}) = 0 \quad (5)$$

Each lysine ion concentration in the equation (5) is calculated from the following equations (6-1) to (6-3). In the equations, $K_{Lys,1}$, $K_{Lys,2}$, and $K_{Lys,3}$ are functions of the temperature obtained from the equations (4-1) to (4-3). In the equations, "$C_{Lys}$" represents the total molar concentration of lysine, i.e. the total molar concentration of lysine molecule (lysine which is not ionized) and lysine ion.

$$C_{Lys^{++}} = \frac{C_{Lys}}{1 + K_{Lys,1}/C_{H^+} + K_{Lys,1} \times K_{Lys,2}/(C_{H^+})^2 + K_{Lys,1} \times K_{Lys,2} \times K_{Lys,3}/(C_{H^+})^3} \quad (6\text{-}1)$$

$$C_{Lys^+} = \frac{C_{Lys}}{1 + C_{H^+}/K_{Lys,1} + K_{Lys,2}/C_{H^+} + K_{Lys,2} \times K_{Lys,3}/(C_{H^+})^2} \quad (6\text{-}2)$$

$$C_{Lys^-} = \frac{C_{Lys}}{1 + C_{H^+}/K_{Lys,3} + (C_{H^+})^2/K_{Lys,2} \times K_{Lys,3} + (C_{H^+})^3/K_{Lys,1} \times K_{Lys,2} \times K_{Lys,3}} \quad (6\text{-}3)$$

The concentrations of carbonate ion and bicarbonate ion in the equation (5) are calculated from the following equations (7-1) to (7-2). In the equations, $K_{CO2,1}$ and $K_{CO2,2}$ are functions of the temperature obtained from the equations (4-4) to (4-5). In the equations, "$C_{CO2}$" represents the total molar concentration of carbon dioxide substances, i.e. the total molar concentration of carbon dioxide molecule, carbonic acid molecule, carbonate ion, and bicarbonate ion.

$$C_{CO_3^{--}} = \frac{C_{CO_2}}{1 + C_{H^+}/K_{CO_2,2} + (C_{H^+})^2/K_{CO_2,1} \times K_{CO_2,2}} \quad (7\text{-}1)$$

$$C_{HCO_3^-} = \frac{C_{CO_2}}{1 + C_{H^+}/K_{CO_2,1} + K_{CO_2,2}/C_{H^+}} \quad (7\text{-}2)$$

The solution ($C_{H^+}$) of the equation (5) was obtained using Newton's method. Specifically, the equation (5) was differentiated, and calculation of $C_{H^+}$ was repeated with Excel, to calculate a stationary $C_{H^+}$.

That is, the following equation (8) was obtained by differentiating the equation (5).

$$\frac{df(C_{H^+})}{dC_{H^+}} = (2 \times dC_{Lys^{++}} + dC_{Lys^+} + dC_{NH4^+}) - (dC_{Lys^-} + dC_{OH^-} + 2 \times dC_{CO3^{--}} + dC_{HCO3^-}) \quad (8)$$

Each parameter in the equation (8) is calculated from the following equations (9-1) to (9-8).

$$\frac{dC_{Lys^{++}}}{dC_{H^+}} = \frac{C_{Lys} \times \{K_{Lys,1}/(C_{H^+})^2 + 2 \times K_{Lys,1} \times K_{Lys,2}/(C_{H^+})^3 + 3 \times K_{Lys,1} \times K_{Lys,2} \times K_{Lys,3}/(C_{H^+})^4\}}{\{1 + K_{Lys,1}/C_{H^+} + K_{Lys,1} \times K_{Lys,2}/(C_{H^+})^2 + K_{Lys,1} \times K_{Lys,2} \times K_{Lys,3}/(C_{H^+})^3\}^2} \quad (9\text{-}1)$$

$$\frac{dC_{Lys^+}}{dC_{H^+}} = \frac{C_{Lys} \times \{-1/K_{Lys,1} + 2 \times K_{Lys,2}/(C_{H^+})^2 + 3 \times K_{Lys,2} \times K_{Lys,3}/(C_{H^+})^3\}}{\{1 + C_{H^+}/K_{Lys,1} + K_{Lys,2}/C_{H^+} + K_{Lys,2} \times K_{Lys,3}/(C_{H^+})^2\}^2} \quad (9\text{-}2)$$

$$\frac{dC_{Lys^-}}{dC_{H^+}} = -\frac{C_{Lys} \times \{1/K_{Lys,3} + 2 \times C_{H^+}/K_{Lys,2} \times K_{Lys,3} - 3 \times (C_{H^+})^2/K_{Lys,1} \times K_{Lys,2} \times K_{Lys,3}\}}{\{1 + C_{H^+}/K_{Lys,3} + (C_{H^+})^2/K_{Lys,2} \times K_{Lys,3} + (C_{H^+})^3/K_{Lys,1} \times K_{Lys,2} \times K_{Lys,3}\}^2} \quad (9\text{-}3)$$

$$\frac{dC_{NH4^+}}{dC_{H^+}} = -\frac{C_{NH4^+} \times K_{NH4^+}}{(C_{H^+})^2 \times (1 + K_{NH4^+}/C_{H^+})^2} \quad (9\text{-}4)$$

$$\frac{dC_{OH^+}}{dC_{H^+}} = -\frac{K_{H2O}}{(C_{H^+})^2} \quad (9\text{-}5)$$

$$\frac{dC_{CO3^{--}}}{dC_{H^+}} = -\frac{C_{CO2} \times (1 + 1/K_{CO2,2} + 2 \times C_{H^+}/K_{CO2,1} \times K_{CO2,2})}{\{1 + C_{H^+}/K_{CO2,2} + (C_{H^+})^2/K_{CO2,1} \times K_{CO2,2}\}^2} \quad (9\text{-}6)$$

$$\frac{dC_{HCO3^-}}{dC_{H^+}} = -\frac{C_{CO2} \times (1 + 1/K_{CO2,1} + K_{CO2,2}/(C_{H^+})^2)}{(1 + C_{H^+}/K_{CO2,1} + K_{CO2,2}/C_{H^+})^2} \quad (9\text{-}7)$$

$$pK_{H_2O} = -\log\left[\exp\left\{45.098 \times \left(1 - \frac{298.15}{(273.18 + Temp.\ [K])}\right)\right\} - 22.477 \times \ln\left\{\frac{(273.18 + Temp.\ [K])}{298.15}\right\} \times 1.004 \times 10^{-14}\right] \quad (9\text{-}8)$$

From the solutions of the equations (5) and (8), the aforementioned calculation was repeated on the basis of the following equation (10) till $C_{H^+}$ became constant. Calculation of the stationary $C_{H^+}$ is carried out for each composition of the fermentation broth and each temperature. That is, herein, the stationary $C_{H^+}$ at each temperature was calculated for the lysine fermentation broth obtained in Reference Example 1 (the composition is shown in Table 4 described later). A change of $C_{H^+}$ when carrying out the repeated calculation for this lysine fermentation broth at 35° C. is shown in FIG. 1.

$$C_{H^+}(x+1) = C_{H^+}(x) - f(C_{H^+})/f(dC_{H^+}) \quad (10)$$

Finally, the pH was calculated on the basis of the following equation (11) using the $C_{H^+}$ value confirmed to be stationary. That is, herein, the pH at each temperature was calculated for the lysine fermentation broth obtained in Reference Example 1 (the composition is shown in Table 4 described later).

$$pH = \log(C_{H^+}) \quad (11)$$

<1-3> Verification of Results of pH Simulation

Figure 2:
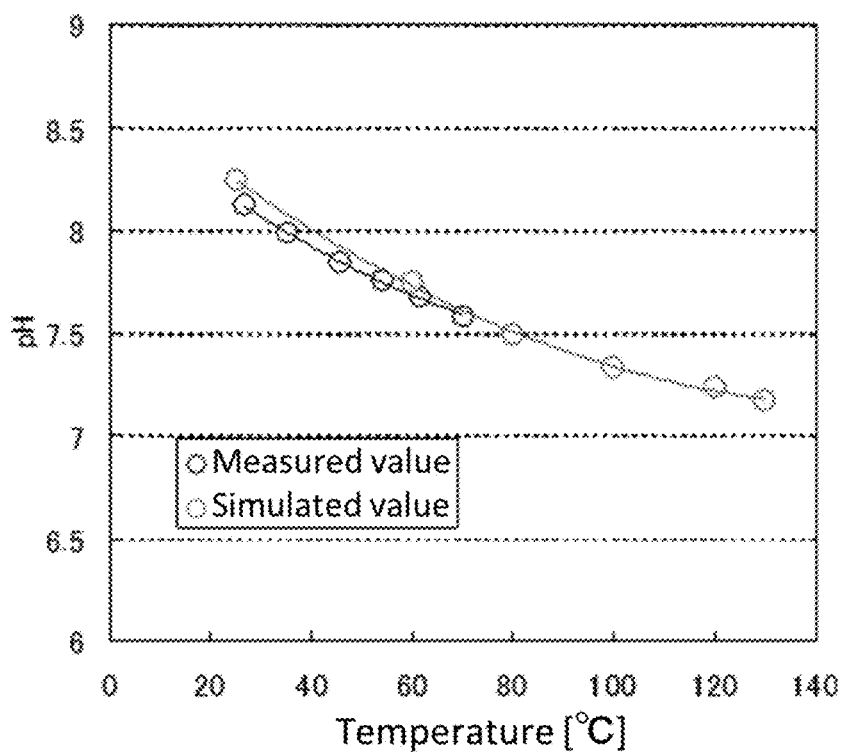
FIG. 2 is a diagram showing measured values and simulated values of pH.

The temperature of the lysine fermentation broth obtained in Reference Example 1 (the composition is shown in Table 4 described later) was adjusted with an oil bath of 120° C., and the pH was measured when the temperature reached a certain temperature (25, 35, 42, 53, 60, and 70° C.). Since it was considered that the composition of the fermentation broth changes if $HCO_3$ contained in the fermentation broth gasifies due to heating, the measurement of the pH was carried out within a temperature range in which foaming was not observed. Specifically, in this experiment, the upper limit was set to 70° C. since foaming was apparently observed under conditions with a temperature of 70° C. or higher. The measured values and the simulated values are shown in FIG. 2. The difference between the measured values and the simulated values was 0.1 or smaller, and that is, a strong correlation was observed between them. From the above, it was considered that the accuracy of this pH simulation is sufficiently high, and the pH of the lysine fermentation broth at each temperature can be roughly calculated by this pH simulation.

Figure 3:
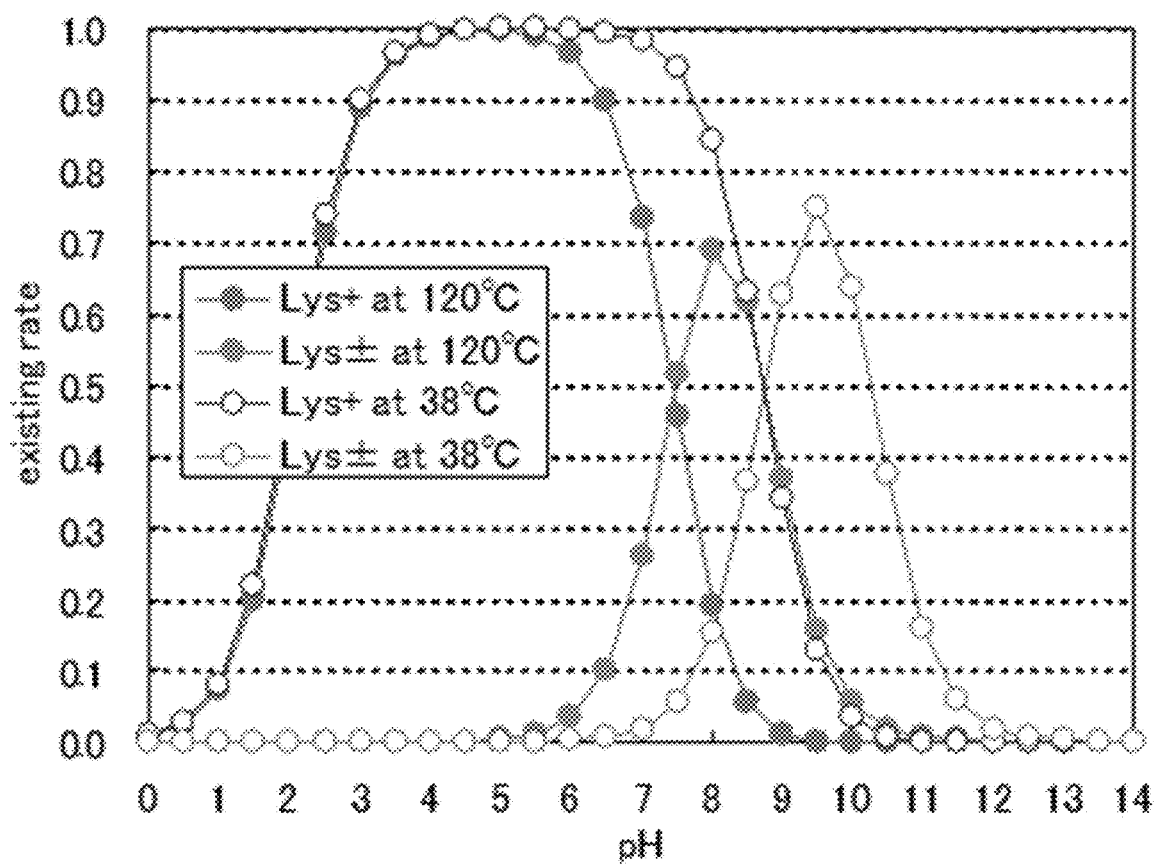
FIG. 3 is a diagram showing dissociation curves of Lys at 38° C. and 120° C.

<2> Construction of Simulator of Required Pressure
<2-1> Assumption for Constructing Simulation Model of Required Pressure A method for roughly calculating the pH based on the composition of the fermentation broth was established in <1>. As a result, using the pK value, which is a function of the temperature, and the pH simulation at an intended temperature, the dissociative state of Lys at the intended temperature can be calculated. As an example, dissociation curves of Lys at 38° C. and 120° C. are shown in FIG. 3. For example, in the case of pH8, while approximately 80% of Lys is electrically charged to be Lys$^+$ at 38° C., the abundance ratio (existing rate) of Lys$^+$ and Lys$^±$ is shifted to be approximately 1:1 at 120° C.

From the results of dissociative state analysis, the following assumption (1) and (2) were obtained.

<Assumption (1)>

Figure 4:
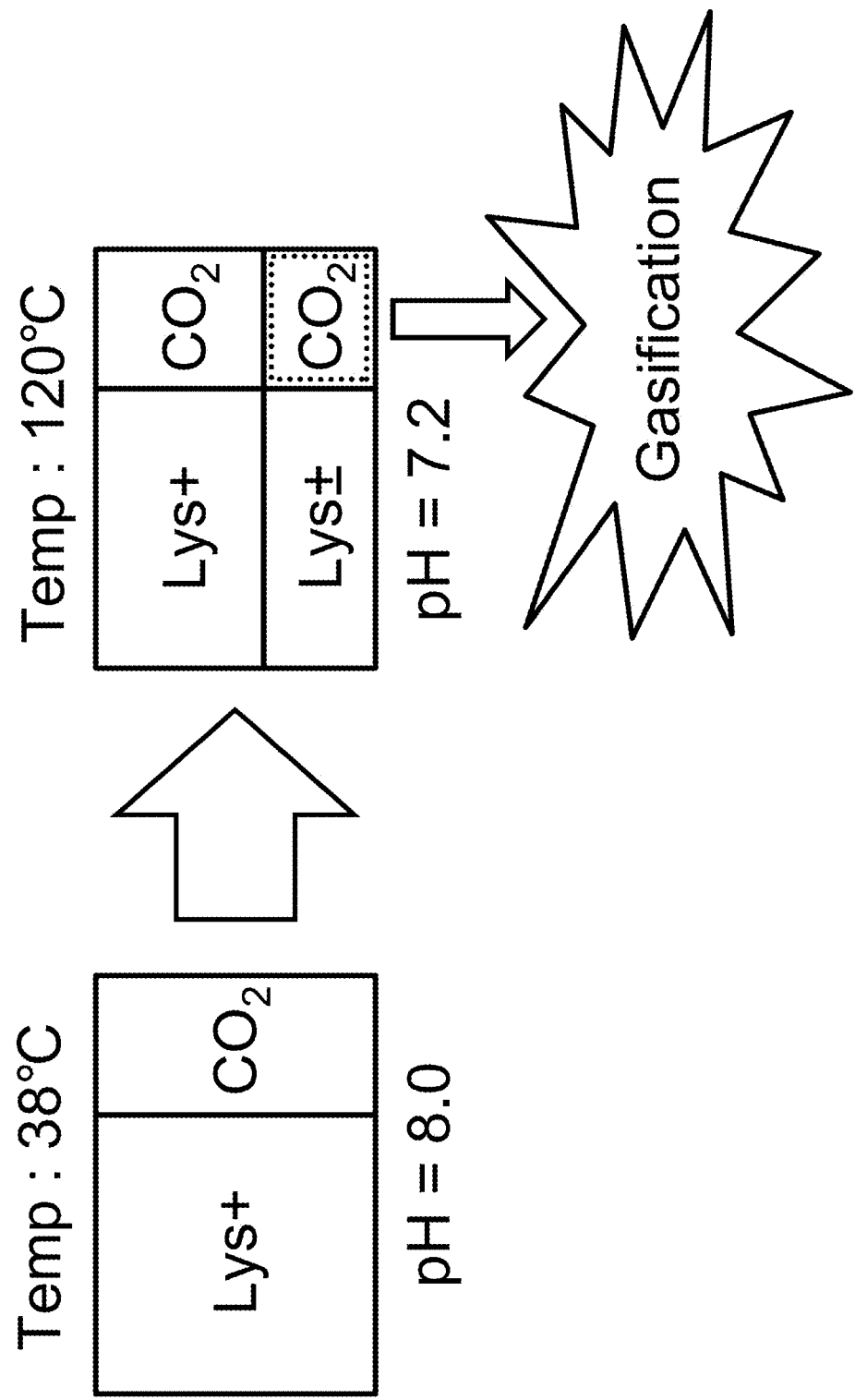
FIG. 4 is a diagram showing images of ion valance at 38° C. and 120° C.

Since Lys is contained in a large amount in the lysine fermentation broth, $HCO_3$ ions are dissolved in the fermentation broth as counter ions of Lys ions in the case of pH8 at 38° C. By contrast, when the lysine fermentation broth is heated to 120° C., approximately half of Lys loses electrical charge to be present as Lys$^±$, and thereby $HCO_3$ ions not retaining Lys as counter ions are generated. It was assumed that these $HCO_3$ ions not retaining Lys gasify. Images of ion valance at 38° C. and 120° C. are shown in FIG. 4.

<Assumption (2)>

It has been known that Henry's law holds for a dilute solution containing a volatile solute. It was assumed that Henry's law holds also for the lysine fermentation broth.

<2-2> Construction of Simulation Model of Required Pressure

Assuming that, on the basis of the assumption (1) and (2), Henry's law holds for $HCO_3$ ions that lost counter ions due to heating, a simulation model for calculating a pressure required for preventing gasification of these $HCO_3$ ions was constructed. The simulation model was constructed for 120° C.

<2-2-1> Calculation of Dissociative State of Lys at 120° C.

Figure 5:
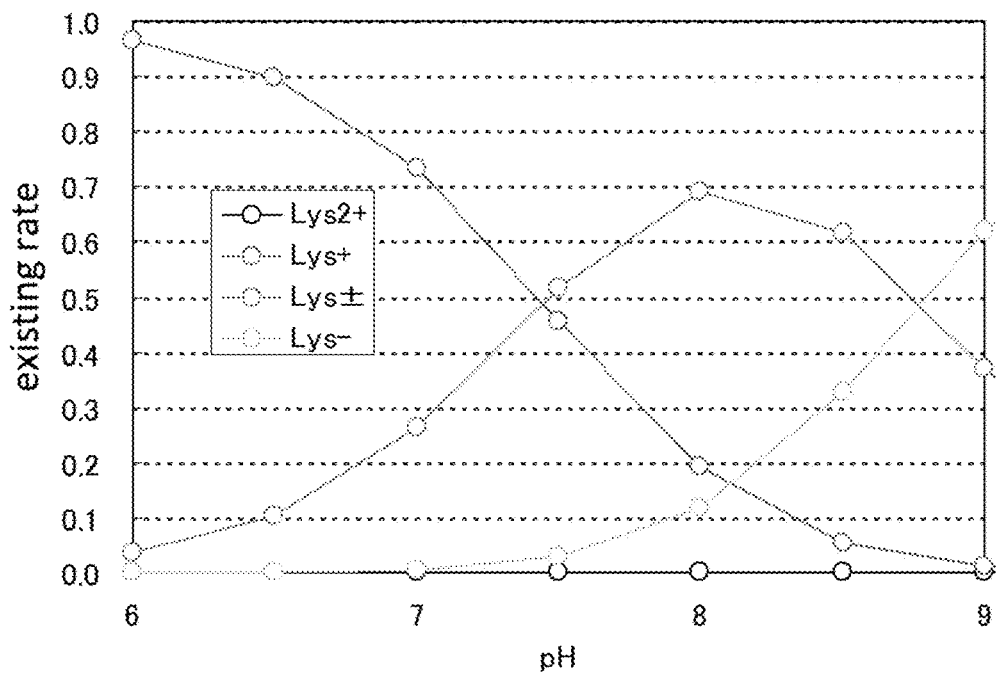
FIG. 5 is a diagram showing the dissociative state of Lys at 120° C.

The dissociative state of Lys at 120° C. is shown in FIG. 5. Since the pH of the lysine fermentation broth used for the simulation is 7 to 7.5 at 120° C. (FIG. 2), the Lys$^+$ abundance ratio at a certain pH from pH7 to pH7.5 was calculated on the basis of the following equation using the dissociative state of Lys at pH7 as the reference on the assumption that the dissociation curve can be linearly approximated within a range from pH7 to pH7.5. The term "Lys$^+$ abundance ratio" refers to the ratio (molar ratio) of Lys$^+$ with respect to total amount of lysine.

$$Lys^+ \text{ abundance ratio} = \left(0.734 - \frac{(0.734 - 0.457)}{0.5} \times (pH - 7)\right) \quad ①$$

<2-2-2> Calculation of Abundance Ratio of $HCO_3$ Ions Not Retaining Counter Ions The abundance ratio of $HCO_3$ ions not retaining counter ions in the lysine fermentation broth heated to 120° C. was calculated on the basis of the following equation. In the equation, "$HCO_3$ concentration" represents the total concentration of $HCO_3$ ions, i.e. the total concentration of $HCO_3$ ions retaining counter ions and $HCO_3$ ions not retaining counter ions. The "$HCO_3$ concentration" can be measured by, for example, ion chromatography. In the equations, "Lys concentration" represents the total concentration of lysine, including both lysine that is ionized and lysine that is not ionized. The term "abundance ratio of $HCO_3$ ions not retaining counter ions" refers to the ratio (molar ratio) of $HCO_3$ ions not retaining counter ions with respect to total amount of $HCO_3$ ions. The term "$HCO_3$ ions not retaining counter ions" referred to herein refers to $HCO_3$ ions that lost counter ions due to heating.

Abundance ratio of $HCO_3$ ions not retaining counter ions = ②

$$\frac{(HCO_3 \text{ concentration}/61 - Lys \text{ concentration}/146.19 \times ①)}{HCO_3 \text{ concentration}/61}$$

<2-2-3> Calculation of Partial Pressure of Carbon Dioxide $P_{CO2}$

The partial pressure of carbon dioxide $P_{CO2}$ was calculated on the basis of the following equation using Henry constant at 120° C. (Aleksander Dhima, Jean-Charles de Hemptinne, and Jacques Jose, Ind. Eng. Chem. Res. 1999, 38, 3144-3161).

$$P_{CO2} = \text{Henry constant} \times 1000 \times HCO_3 \text{ concentration}/44 \times 10 \times ② / 55.5 \quad ③$$

<2-2-4> Calculation of Partial Pressure of Water Vapor

The partial pressure of water vapor $P_{H2O}$ was calculated on the basis of the following equation using the Wagner equation.

$$\ln(P/Pc) = \frac{(-A \times \tau + B \times \tau^{1.5} - C \times \tau^3 - D \times \tau^6)}{(T/Tc)} \quad ④$$

$$\tau = 1 - \frac{T(K)}{Tc} \quad ⑤$$

$A = 7.76451$ $B = 1.45838$ $C = 2.7758$ $D = 1.23303$ $Tc = 647.3$ [K]

$Pc = 22120$ [kPa]

$P_{H_2O} = \exp(\ln(P/Pc)) \times Pc$

<2-2-5> Calculation of Required Pressure

The required pressure P was calculated on the basis of the following equation.

Required pressure $P = ③ + ⑤$ ⑥

Example 3

Comparative Verification of Experimental Values and Calculated Values of Pressure Required for Preventing Generation of Carbon Dioxide Gas from Lysine Fermentation Broth <1> Calculation of Calculated Values For the lysine fermentation broth (pH8.3) obtained in Reference Example 1, the pressure required for preventing generation of carbon dioxide gas from the fermentation broth was calculated in a range from 60° C. to 130° C. on the basis of the equation shown in Example 2. The composition of this lysine fermentation broth is shown in Table 4.

TABLE 4

| Composition of fermentation broth [%] | |
|---|---|
| Lysine | 13.93 |
| $CO_2$ | 2.51 |
| Ammonia | 0.08 |
| Potassium | 0.06 |
| Magnesium | 0.04 |
| Chloride ion | 0.08 |
| Sulfate ion | 0.12 |
| Succinic acid | 0.22 |
| Acetic acid | 0.18 |

<2> Measurement of Experimental Values

The lysine fermentation broth (pH8.3) obtained in Reference Example 1 was put in a high pressure and high temperature reactor (TEM-V, Taiatsu Techno) so that the porosity of apparatus (the ratio of the gas phase) comes to be 6% v/v, sealed, and heated to 60° C., 80° C., 100° C., 105° C., 110° C., 115° C., 120° C., 125° C., and 130° C. The pressure of the gas phase was measured at each of those temperatures, and regarded as the pressure required for preventing generation of carbon dioxide gas from the fermentation broth at that temperature.

<3> Comparison Between Experimental Values and Calculated Values

Figure 6:
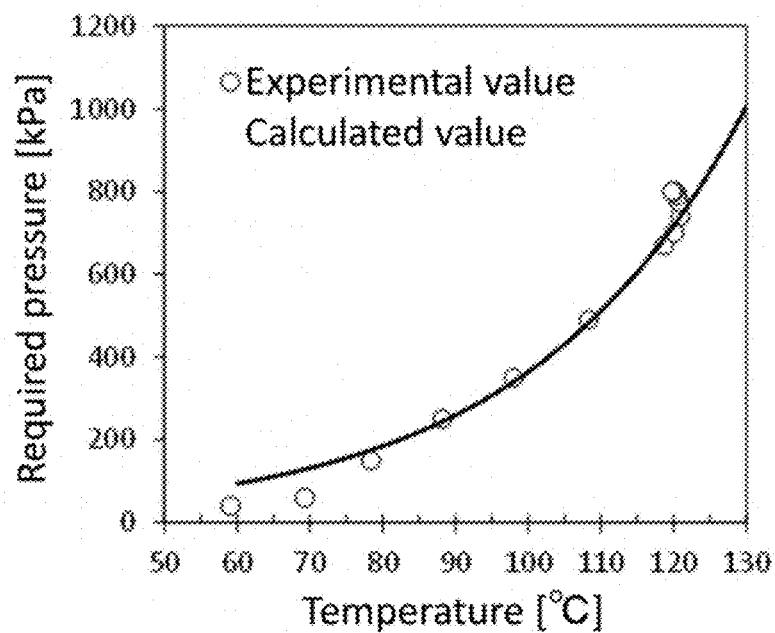
FIG. 6 is a diagram showing calculated values and experimental values of pressure sufficient for preventing generation of carbon dioxide gas from a fermentation broth.

The calculated values and the experimental values are shown in FIG. 6. The calculated values and the experimental values well agreed with each other. Hence, it was indicated that the equation shown in Example 2 is usable for calculating the pressure required for preventing generation of carbon dioxide gas from the fermentation broth.

Example 4

Figure 7:
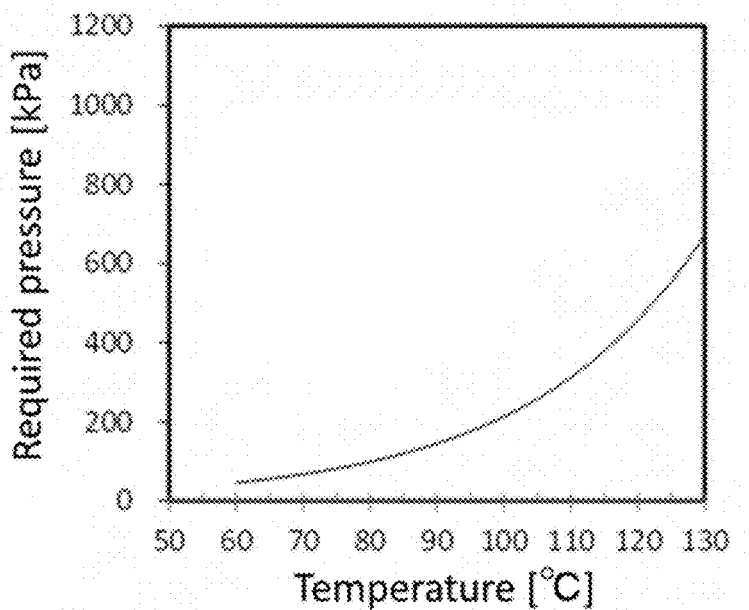
FIG. 7 is a diagram showing an approximate equation of pressure sufficient for preventing generation of carbon dioxide gas from a fermentation broth, the equation obtained for a model lysine fermentation broth (lysine concentration, 11 g/dl; pH9.0).

Calculation Example of Pressure Required for Preventing Generation of Carbon Dioxide Gas from Lysine Fermentation Broth For a model lysine fermentation broth (lysine concentration, 11 g/dl; pH9.0) shown in Table 5, the pressure required for preventing generation of carbon dioxide gas from the fermentation broth was calculated in a range from 25° C. to 130° C. on the basis of the equation shown in Example 2. The calculation results were converted to an approximate equation, and the obtained approximate equation is shown in FIG. 7. In the case of the model lysine fermentation broth used in this Example (lysine concentration, 11 g/dl; pH9.0), since the pH is higher and the lysine concentration is lower than the case of the lysine fermentation broth used in Example 3 (lysine concentration, 13.93 g/dl; pH8.3), the concentration of required $CO_2$ is low, and hence, the pressure required for preventing generation of carbon dioxide gas from lysine fermentation broth was also calculated to be low. According to this approximate equation, the required pressure was expressed as follows.

Required pressure=$1.99 \times 10^{-3} \times \text{temperature}^{2.54}$

TABLE 5

| Composition of fermentation broth [%] | |
|---|---|
| Lysine | 11.5 |
| $CO_2$ | 0.80 |
| Ammonia | 0.08 |
| Potassium | 0.06 |
| Magnesium | 0.04 |
| Chloride ion | 0.08 |

TABLE 5-continued

| Composition of fermentation broth [%] | |
|---|---|
| Sulfate ion | 0.12 |
| Succinic acid | 0.22 |
| Acetic acid | 0.18 |

Example 5

Suppression of Decrease in Lysine Concentration During Decarboxylation After Pressurized Heat Treatment The lysine fermentation broth (pH8.3) obtained in Reference Example 1 was put in a reactor, subject to a pressurized heat treatment in a retention pipe (retention tube) at 120° C. and 0.1 MPa, and then heated at 60° C. for 24 hours under atmospheric pressure. As a control, the lysine fermentation broth (pH8.3) obtained in Reference Example 1 was heated at 60° C. for 24 hours under atmospheric pressure without being subject to a pressurized heat treatment. Transition of the lysine concentration was confirmed for each condition. The results are shown in Table 6. It was shown that by subjecting the fermentation broth to a pressurized heat treatment, a decrease in the lysine concentration during a subsequent purification process can be suppressed.

TABLE 6

Effect of high temperature and high pressure treatment on decrease in lysine concentration

| | Lysine concentration (concentration/initial concentration) | | |
|---|---|---|---|
| | fermentation broth | After pressurized heat treatment | After heating at 60° C. |
| With high temperature and high pressure treatment | 1.0 | 1.0 | 1.0 |
| Without high temperature and high pressure treatment | 1.0 | — | $9.4 \times 10^{-1}$ |

INDUSTRIAL APPLICABILITY

According to the present invention, a decrease in the contained amount of a basic amino acid in a fermentation broth obtainable by the carbonate fermentation can be prevented, and thereby the basic amino acid or a fermentation product containing the same can be efficiently produced.

The invention claimed is:

1. A method for producing a basic amino acid or a fermentation product containing the basic amino acid, the method comprising:
    (A) culturing a microorganism able to produce a basic amino acid in a culture medium so that bicarbonate ions and/or carbonate ions serve as counter ions for the basic amino acid, to obtain a fermentation broth containing the basic amino acid; and
    (B) heat treating the fermentation broth under a pressure sufficient to prevent generation of carbon dioxide gas from the fermentation broth.

2. The method according to claim 1,
    wherein said pressure is gauge pressure and is equal to or higher than the total value of the partial pressure of carbon dioxide and the partial pressure of water vapor at the temperature of said heat treatment, and wherein said partial pressure of carbon dioxide is determined using the concentrations of the basic amino acid, $CO_2$, $NH_3$, K, Mg, Cl, $SO_4$, acetic acid, and succinic acid in the fermentation broth and the temperature of the heat treating as variables.

3. The method according to claim 1, wherein said pressure is gauge pressure and is equal to or higher than the pressure shown in the following equation:

$$\text{Pressure (kPa)} = 1.99 \times 10^{-3} \times T^{2.54}$$

wherein T is the temperature in centigrade of the heat treating.

4. The method according to claim 1, wherein said pressure is gauge pressure and is equal to or higher than the pressure of a gas phase in a sealed vessel observed when the fermentation broth is put in the sealed vessel so that the porosity of said vessel becomes 6% v/v and adjusted to the temperature of said heat treating.

5. The method according to claim 1, wherein said pressure is gauge pressure and is 400 kPa or higher.

6. The method according to claim 1, wherein said pressure is gauge pressure and is 1000 kPa or higher.

7. The method according to claim 1, wherein the temperature of the heat treating is 80° C. to 130° C.

8. The method according to claim 1, wherein the temperature of the heat treating is 100° C. to 130° C.

9. The method according to claim 1, wherein said heat treating is carried out in a pressure vessel under conditions wherein substantially no gas phase is present in the pressure vessel.

10. The method according to claim 1, further comprising: decarboxylating the fermentation broth after said heat treating.

11. The method according to claim 1, wherein said culturing is carried out while controlling the pH of the culture medium to 7.2 to 9.0 during at least a partial period of culture.

12. The method according to claim 1, wherein said culturing is carried out so that the pH of the culture medium at the completion of culture is 7.2 or higher.

13. The method according to claim 1, wherein said culturing is carried out so that bicarbonate ions and/or carbonate ions are present in the culture medium at a concentration of 20 mM or more during at least a partial period of culture by controlling the internal pressure of a fermentation tank to be positive and/or by supplying carbon dioxide gas into the culture medium.

14. The method according to claim 1, wherein said culturing is carried out so that the concentration of anions other than bicarbonate ions and/or carbonate ions in the culture medium is 900 mM or lower.

15. The method according to claim 13, wherein the internal gauge pressure of the fermentation tank is 0.03 to 0.2 MPa.

16. The method according to claim 1, wherein said culturing is carried out so that the total ammonia concentration in the culture medium is controlled to 300 mM or lower during at least a partial period of culture.

17. The method according to claim 1, wherein the basic amino acid is L-lysine.

18. The method according to claim 1, wherein the microorganism is a coryneform bacterium or *Escherichia coli*.

19. The method according to claim 1, wherein the fermentation product is selected from the group consisting of the fermentation broth, a supernatant of the fermentation broth, a decarboxylation product of the fermentation broth, a concentrated product of the fermentation broth, a dried product of the fermentation broth, and a processed product of the fermentation broth.

* * * * *